(12) United States Patent
Hinze et al.

(10) Patent No.: US 8,053,576 B2
(45) Date of Patent: Nov. 8, 2011

(54) COMPOSITIONS CONTAINING SPIROCYCLIC CYCLOHEXANE COMPOUNDS

(75) Inventors: Claudia Hinze, Aachen (DE); Otto Aulenbacher, Herzogenrath (DE); Bernd Sundermann, Aachen (DE); Stefan Oberboersch, Aachen (DE); Elmar Friderichs, Stolberg (DE); Werner Englberger, Stolberg (DE); Babette-Yvonne Koegel, Langerwehe-Hamich (DE); Klaus Linz, Bonn (DE); Hans Schick, Berlin (DE); Helmut Sonnenschein, Berlin (DE); Birgitta Henkel, Berlin (DE); Valerie Sarah Rose, Essex (GB); Michael Jonathan Lipkin, Essex (GB)

(73) Assignee: Gruenenthal GmbH, Aachen (DE)

( * ) Notice: Subject to any disclaimer, the term of this patent is extended or adjusted under 35 U.S.C. 154(b) by 51 days.

(21) Appl. No.: 12/372,340

(22) Filed: Feb. 17, 2009

(65) Prior Publication Data

US 2009/0156626 A1 Jun. 18, 2009

Related U.S. Application Data

(60) Division of application No. 11/126,139, filed on May 11, 2005, now Pat. No. 7,547,707, which is a continuation of application No. PCT/EP2003/012305, filed on Nov. 5, 2003.

(30) Foreign Application Priority Data

Nov. 11, 2002 (DE) ................................ 102 52 667

(51) Int. Cl.
C07D 407/04 (2006.01)
C07D 339/08 (2006.01)
C07D 487/08 (2006.01)
A61K 31/4353 (2006.01)

(52) U.S. Cl. ................ 546/18; 549/15; 549/24; 549/31; 549/330; 549/333; 549/336; 514/278; 548/421

(58) Field of Classification Search ...... 546/18; 549/15, 24, 31, 330, 333, 336; 514/278; 548/421

See application file for complete search history.

(56) References Cited

U.S. PATENT DOCUMENTS

| | | | |
|---|---|---|---|
| 3,328,412 A | 6/1967 | Atkinson et al. | |
| 3,843,681 A | 10/1974 | Demerson et al. | |
| 4,021,451 A | 5/1977 | Dobson et al. | |
| 4,291,039 A | 9/1981 | Van Dyke, Jr. et al. | |
| 4,575,508 A | 3/1986 | Steiner et al. | |
| 5,328,905 A | 7/1994 | Hamminga et al. | |
| 5,631,265 A | 5/1997 | Audia et al. | |
| 5,760,051 A | 6/1998 | Audia et al. | |
| 5,869,691 A | 2/1999 | Audia et al. | |
| 6,586,445 B1 | 7/2003 | Thurieau et al. | |
| 7,314,886 B2 | 1/2008 | Chao et al. | |
| 7,332,519 B2 | 2/2008 | Hinze et al. | |
| 7,446,122 B2 | 11/2008 | Chao et al. | |
| 7,485,634 B2 | 2/2009 | Martin et al. | |
| 7,547,707 B2 | 6/2009 | Hinze et al. | |
| 7,595,311 B2 | 9/2009 | Busch et al. | |
| 2004/0038970 A1 | 2/2004 | Thurieau et al. | |
| 2006/0235012 A1 | 10/2006 | Davidson et al. | |
| 2007/0149557 A1 | 6/2007 | Collins et al. | |
| 2008/0280942 A1 | 11/2008 | Diaz-Fernandez et al. | |
| 2009/0042866 A1 | 2/2009 | Lennox et al. | |
| 2009/0326218 A1 | 12/2009 | Martin et al. | |

FOREIGN PATENT DOCUMENTS

| | | |
|---|---|---|
| DE | 2 226 340 A | 3/1973 |
| EP | 0 466 548 A1 | 1/1992 |
| EP | 1 142 587 A1 | 10/2001 |
| GB | 1055203 A | 1/1967 |
| WO | WO 99 64420 A1 | 12/1999 |

OTHER PUBLICATIONS

German Search Report dated Jul. 14, 2003 w/partial English translation (eight (8) pages).

John P. Mayer, et al., "Application of the Pictet-Splenger Reaction in Combinatorial Chemistry", Tetrahedron Letters, 1996, pp. 5633-5636, vol. 37, No. 32, Elsevier Science Ltd., printed in Great Britain, PII: S0040-4039(96)01219-1.

T. Nagy, et al., "Synthesis and Analgesic Evaluation of Some 1, 1-Disubstituted 3-Carboxy-4-Phenyl-1, 2, 3, 4-Tetrahydro-β-Carboline Derivatives", Eur. J. Med. Chem., 1995, pp. 575-586, vol. 30, Elsevier, Paris, France.

International Search Report dated Feb. 23, 2004 w/partial English translation (five (5) pages).

Joerg Berg et al., "Isoenzyme-Specific Cyclooxygenase Inhibitors: A Whole Cell Assay System Using the Human Erythroleukemic Cell Line HEL and the Human Monocytic Cell Line Mono Mac 6", Journal of Pharmacological and Toxicological Methods 37, vol. No. 4, 179-186 (1997), Elsevier Science Inc., New York.

Fuad A. Abdulla et al., "Axotomy Reduces the Effect of Analgesic Opioids Yet Increases the Effect of Nociceptin on Dorsal Root Ganglion Neurons", The Journal of Neuroscience, Dec. 1, 1998, 18(23): 9685-9694.

(Continued)

Primary Examiner — Rita Desai
(74) Attorney, Agent, or Firm — Crowell & Moring LLP

(57) ABSTRACT

Spirocyclic cyclohexane compounds corresponding to formula I

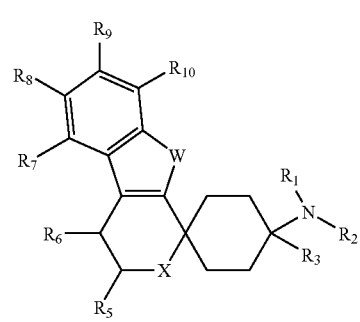

a method for producing them, pharmaceutical compositions containing them, and methods of using them.

10 Claims, No Drawings

OTHER PUBLICATIONS

Anthony L. Beck et al., "Synthesis of 3,4-Bridged Indoles by Photocyclisation Reactions. Part 2.[1] Photocyclisation of Halogenoacetyl Tryptophol Derivatives and α-Chloro Indol-3-ylalkanoate Esters", J. Chem. Soc. Perkin Trans. 1, pp. 813-821, 1992.

Girolamo Calo et al., "Pharmacology of nociceptin and Its receptor: a novel therapeutic target", British Journal of Pharmacology (2000) 129, 1261-1283, Macmillan Publishers Ltd.

E. Campaigne et al., "Benzo[b]thiophene Derivatives. VII. An Abnormal Substitution Product From 3-Chloromethylbenzo[b]thiophene (1)", Chemistry Laboratories, pp. 231-235, Indiana University, Sep. 1965.

Simon M. N. Efange et al., "Modified Ibogaine Fragments: Synthesis and Preliminary Pharmacological Characterization of 3-Ethyl-5-phenyl-1,2,3,4,5,6-hexahydroazepino[4,5-b]benzothiophenes", J. Med. Chem. 1998, 41, 4486-4491.

John W. Ellingboe et al., "Antihyperglycemic Activity of Novel Substituted 3H-1,2,3,5-Oxathiadiazole 2-Oxides", J. Med. Chem. 1992, 35, 1176-1183.

Simon J. Garden et al., "A versatile synthetic methodology for the synthesis of tryptophols", Tetrahedron 58 (2002) 8399-8412, Pergamon.

L. C. Hendershot et al., "Antagonism of the Frequency of Phenylquinone-Induced Writhing in the Mouse by Weak Analgesics and Nonanalgesics", vol. 125, pp. 237-240, The Biochemical Research Laboratory, The Dow Chemical Company, Midland, Michigan, Received for publication Sep. 19, 1958.

Francois Jenck et al., "Orphanin FQ acts as an anxiolytic to attenuate behavioral responses to stress", Proc. Natl. Acad. Sci. USA, vol. 94, pp. 14854-14858, Dec. 1997, Neurobiology.

I. Jirkovsky et al., "Synthesis of 1,3,4,9-Tetrahydro-1-alkylthiopyrano [3,4-b] indole-1-acetic Acids. The Sulfur Isoster of Prodolic Acid", vol. 12, pp. 937-940, Ayerst Research Laboratories, Montreal, Quebec, Canada, Oct. 1975.

Michael A. King et al., "Spinal analgesic activity of orphanin FQ/nociceptin and its fragments"Neuroscience Letters 223 (1997) 113-116, Elsevier Science Letters.

Daniel Lednicer et al., "4-Amino-4-arylcyclohexanones and Their Derivatives, a Novel Class of Analgesics. 1. Modification of the Aryl Ring", The Upjohn Company, Research Laboratories, Kalamazoo, Michigan, Received Aug. 7, 1979.

Toshiya Manabe et al., "Facilitation of long-term potentiation and memory in mice lacking nociceptin receptors", Letters to Nature, vol. 394, pp. 577-581, Aug. 6, 1998, Macmillan Publishers Ltd.

Jean-Claude Meunier et al., "Isolation and structure of the endogenous agonist of opioid receptor-like $ORL_1$ receptor" Letters of Nature, vol. 377, pp. 532-535, Oct. 12, 1995.

J. S. Mogil et al., "Orphanin FQ is a Functional Anti-Opioid Peptide", Letter to Neuroscience, Neuroscience vol. 75, No. 2, pp. 333-337, 1996, Elsevier Science Ltd., Pergamon, Great Britain.

Miyuki Nishi et al., "Unrestrained nociceptive response and disregulation of hearing ability in mice lacking the nociceptin/orphaninFQ receptor", The EMBO Journal, vol. 16, No. 8, pp. 1858-1864, 1997, Oxford University Press.

James R. Pearson et al., "Vinylindenes and Some Heteroanalogues in the Diels-Alder Reaction. IX* 3-Vinylbenzofuran and 1,4-Naphthoquinone", Aust. J. Chem., 1991, 44, 907-917.

Rainer K. Reinscheid et al., "Orphanin FQ: A Neuropeptide That Activates an Opioidlike G Protein-Coupled Receptor", Science, vol. 270, pp. 792-794, Nov. 3, 1995.

Shuichi Yokohama et al., "Synthesis and Antiallergy Activity of [1,3,4] Thiadiazolo[3,2-a]-1,2,3-triazolo[4,5-d] pyrimidin-9(3H)-one Derivatives. II.[1,2]6-Alkyl- and 6-Cycloalkylalkyl Derivatives", Chem. Pharm. Bull., Vo. 40, No. 9, pp. 2391-2398, Sep. 1992.

Donald Zaragoza, "Side Reactions in Organic Synthesis", (preface and pp. 8 and 9) 2005.

Chang et al., Molecular Pharmacology, 26, 484-488, 1984.

Erchegyi at al., Journal of Medicinal Chemistry 2003, 46, 5587-5596.

Bignan et al., Bioorganic & Medicinal Chemistry Letters 2005, 15, 5022-5026.

COMPOSITIONS CONTAINING SPIROCYCLIC CYCLOHEXANE COMPOUNDS

CROSS REFERENCE TO RELATED APPLICATIONS

This application is a division of patent application Ser. No. 11/126,139, filed May 11, 2005, now U.S. Pat. No. 7,547,707, which in turn was a continuation of international patent application no. PCT/EP2003/012305, filed Nov. 5, 2003 designating the United States of America, and published in German on May 27, 2004 as WO 2004/043967, the entire disclosure of which is incorporated herein by reference. Priority is claimed based on Federal Republic of Germany patent application no. DE 102 52 667.2, filed Nov. 11, 2002.

BACKGROUND OF THE INVENTION

The present invention relates to spirocyclic cyclohexane derivatives, processes for their preparation, medicaments comprising these compounds and the use of spirocyclic cyclohexane derivatives for the preparation of medicaments.

The heptadecapeptide nociceptin is an endogenous ligand of the ORL1 (opioid receptor-like) receptor (Meunier et al., Nature 377, 1995, p. 532-535), which belongs to the family of opioid receptors and is to be found in many regions of the brain and spinal cord, and has a high affinity for the ORL1 receptor. The ORL1 receptor is homologous to the µ, κ and δ opioid receptors and the amino acid sequence of the nociceptin peptide has a marked similarity to those of the known opioid peptides. The receptor activation induced by nociceptin leads, via coupling with $G_{i/o}$ proteins, to an inhibition of adenylate cyclase (Meunier et al., Nature 377, 1995, p. 532-535).

The nociceptin peptide shows a pronociceptive and hyperalgesic activity after intercerebroventicular administration in various animal models (Reinscheid et al., Science 270, 1995, p. 792-794). These findings can be explained as an inhibition of stress-induced analgesia (Mogil et al., Neuroscience 75, 1996, p. 333-337). In this connection, it has also been possible to demonstrate an anxiolytic activity of nociceptin (Jenck et al., Proc. Natl. Acad. Sci. USA 94, 1997, 14854-14858).

On the other hand, it has also been possible to demonstrate an antinociceptive effect of nociceptin in various animal models, in particular after intrathecal administration. Nociceptin has an antinociceptive action in various pain models, for example in the tail flick test in the mouse (King et al., Neurosci. Lett., 223, 1997, 113-116. It has likewise been possible to demonstrate an antinociceptive action of nociceptin in models for neuropathic pain, which is of particular interest inasmuch as the activity of nociceptin increases after axotomy of spinal nerves. This is in contrast to conventional opioids, the activity of which decreases under these conditions (Abdulla and Smith, J. Neurosci., 18, 1998, p. 9685-9694).

The ORL1 receptor is moreover also involved in regulation of further physiological and pathophysiological processes. These include, inter alia, learning and memory development (Manabe et al., Nature, 394, 1997, p. 577-581), audition (Nishi et al., EMBO J., 16, 1997, p. 1858-1864) and numerous further processes. A review article by Calo et al. (Br. J. Pharmacol., 129, 2000, 1261-1283) gives an overview of the indications or biological processes in which the ORL1 receptor plays a role or with high probability could play a role. This mentions, inter alia: analgesia, stimulation and regulation of food intake, influence on µ-agonists, such as morphine, treatment of withdrawal symptoms, reduction in the addiction potential of opioids, anxiolysis, modulation of motor activity, impaired memory, epilepsy; modulation of neurotransmitter secretion, in particular glutamate, serotonin and dopamine, and therefore neurodegenerative diseases; influencing of the cardiovascular system, initiation of an erection, diuresis, antinatriuresis, electrolyte balance, arterial blood pressure, water retention diseases, intestinal motility (diarrhea), relaxing effects on the respiratory tract, micturation reflex (urinary incontinence). The use of agonists and antagonists as anoretics, analgesics (also in co-administration with opioids) or nootropics is furthermore discussed.

The possible uses of compounds which bind to the ORL1 receptor and activate or inhibit this are correspondingly diverse. Alongside this, however, opioid receptors, such as the µ-receptor, but also the other sub-types of these opioid receptors, namely δ and κ, play a large role precisely in the area of pain therapy, but also in that of other indications of those mentioned. Accordingly, it is favourable if the compound also show an action on these opioid receptors.

SUMMARY OF THE INVENTION

The object of the present invention was to provide medicaments which act on the nociceptin/ORL1 receptor system and are therefore suitable for medicaments, in particular for treatment of the various diseases associated, according to the prior art, with this system and for use in the indications mentioned there.

The invention therefore provides spirocyclic cyclohexane derivatives of the general formula I

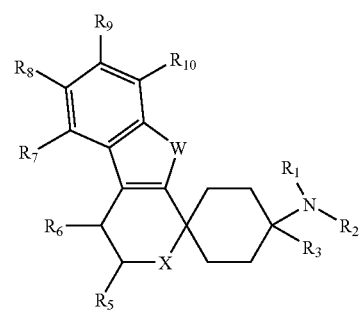

wherein $R^1$ and $R^2$ independently of one another represent H; CHO; $C_{1-5}$-alkyl in each case saturated or unsaturated, branched or unbranched, mono- or polysubstituted or unsubstituted; $C_{3-8}$-cycloalkyl, in each case saturated or unsaturated, mono- or polysubstituted or unsubstituted; or aryl, $C_{3-8}$-cycloalkyl or heteroaryl which are bonded via $C_{1-3}$-alkyl and are in each case mono- or polysubstituted or unsubstituted; or $R^1$ and $R^2$ together represent $CH_2CH_2OCH_2CH_2$, $CH_2CH_2NR^{11}CH_2CH_2$ or $(CH_2)_{3-6}$
wherein
$R^{11}$ denotes H; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl-, or heteroaryl, in each case mono- or polysubstituted or unsubstituted; or aryl, $C_{3-8}$-cycloalkyl or heteroaryl which are bonded via $C_{1-3}$-alkyl and are in each case mono- or polysubstituted or unsubstituted;

$R^3$ represents $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl, in each case unsubstituted or mono- or polysubstituted; aryl or $C_{3-8}$-cycloalkyl which are bonded via $C_{1-3}$-alkyl group and are in each case unsubstituted or mono- or polysubstituted;

W represents $NR^4$, O or S
wherein
$R^4$ represents H; $C_{1-5}$-alkyl, saturated or unsaturated, branched or unbranched, unsubstituted or mono- or polysubstituted; aryl, or heteroaryl, in each case substituted or unsubstituted; aryl, heteroaryl or cycloalkyl which are bonded via a $C_{1-3}$-alkyl group and are in each case mono- or polysubstituted or unsubstituted; $COR^{12}$; $SO_2R^{12}$,
wherein
$R^{12}$ denotes H; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl-, or heteroaryl, in each case mono- or polysubstituted or unsubstituted; or aryl, $C_{3-8}$-cycloalkyl or heteroaryl which are bonded via $C_{1-3}$-alkyl and are in each case mono- or polysubstituted or unsubstituted; $OR^{13}$; $NR^{14}R^{15}$;

$R^5$ represents =O; H; $C_{1-5}$-alkyl, saturated or unsaturated, branched or unbranched, unsubstituted or mono- or polysubstituted; $COOR^{13}$, $CONR^{13}$, $OR^{13}$; $C_{3-8}$-cycloalkyl, saturated or unsaturated, unsubstituted or mono- or polysubstituted; aryl-, or heteroaryl, unsubstituted or mono- or polysubstituted; or aryl, $C_{3-8}$-cycloalkyl or heteroaryl which are bonded $C_{1-3}$-alkyl and are unsubstituted or mono- or polysubstituted;

$R^6$ represents H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, saturated or unsaturated, branched or unbranched, unsubstituted or mono- or polysubstituted; $C_{3-8}$-cycloalkyl, saturated or unsaturated, unsubstituted or mono- or polysubstituted; aryl-, or heteroaryl, unsubstituted or mono- or polysubstituted; or aryl, $C_{3-8}$-cycloalkyl or heteroaryl which are bonded via $C_{1-3}$-alkyl and are unsubstituted or mono- or polysubstituted; or $R^5$ and $R^6$ together denote $(CH_2)_n$, where n=2, 3, 4, 5 or 6, wherein individual hydrogen atoms can also be replaced by F, Cl, Br, I, $NO_2$, $CF_3$, $OR^{13}$, CN or $C_{1-5}$-alkyl;

$R^7$, $R^8$, $R^9$ and $R^{10}$ independently of one another represent H, F, Cl, Br, I, $NO_2$, $CF_3$, $OR^{13}$, $SR^{13}$, $SO_2R^{13}$, $SO_2OR^{13}$, $SO_2NH_2$, CN, $COOR^{13}$, $NR^{14}R^{15}$; $C_{1-5}$-alkyl, $C_{3-8}$-cycloalkyl, unsubstituted or mono- or polysubstituted; aryl-, or heteroaryl, unsubstituted or mono- or polysubstituted; or aryl, $C_{3-8}$-cycloalkyl or heteroaryl which are bonded via $C_{1-3}$-alkyl and are unsubstituted or mono- or polysubstituted;
wherein
$R^{13}$ denotes H; $C_{1-5}$-alkyl in each case saturated or unsaturated, branched or unbranched, unsubstituted or mono- or polysubstituted; $C_{3-8}$-cycloalkyl, in each case saturated or unsaturated, unsubstituted or mono- or polysubstituted; aryl-, or heteroaryl, unsubstituted or mono- or polysubstituted; or aryl, $C_{3-8}$-cycloalkyl or heteroaryl which are bonded via $C_{1-3}$-alkyl and are unsubstituted or mono- or polysubstituted;

$R^{14}$ and $R^{15}$ independently of one another denote H; $C_{1-5}$-alkyl, in each case saturated or unsaturated, branched or unbranched, unsubstituted or mono- or polysubstituted; or $C_{3-8}$-cycloalkyl, in each case saturated or unsaturated, unsubstituted or mono- or polysubstituted; aryl-, or heteroaryl, unsubstituted or mono- or polysubstituted; or aryl, $C_{3-8}$-cycloalkyl or heteroaryl which are bonded via $C_{1-3}$-alkyl and are unsubstituted or mono- or polysubstituted; or $R^{14}$ and $R^{15}$ together form $CH_2CH_2OCH_2CH_2$, $CH_2CH_2NR^{16}CH_2CH_2$ or $(CH_2)_{3-6}$,
wherein
$R^{16}$ denotes H; $C_{1-5}$-alkyl saturated or unsaturated, branched or unbranched, unsubstituted or mono- or polysubstituted;

X represents O, S, SO, $SO_2$ or $NR^{17}$;
wherein
$R^{17}$ denotes H; $C_{1-5}$-alkyl, saturated or unsaturated, branched or unbranched; $COR^{12}$ or $SO_2R^{12}$, in the form of the racemate; the enantiomers, diastereomers, mixtures of the enantiomers or diastereomers or an individual enantiomer or diastereomer; or the bases and/or salts of physiologically acceptable acids or cations.

Where various radicals are combined, for example $R^7$, $R^8$, $R^9$ and $R^{10}$, and radicals on substituents thereof are combined, such as e.g. $OR^{13}$, $SR^{13}$, $SO2R^{13}$ or $COOR^{13}$, one substituent, e.g. $R^{13}$, can assume different meanings for two or more radicals, for example $R^7$, $R^8$, $R^9$ and $R^{10}$, within a substance.

The compounds according to the invention show good binding to the ORL1 receptor, but also to other opioid receptors.

In the context of this invention, the expressions "$C_{1-5}$-alkyl" and "$C_{1-3}$-alkyl" include acyclic saturated or unsaturated hydrocarbon radicals, which can be branched- or straight-chain and unsubstituted or mono- or polysubstituted, having 1, 2, 3, 4 or 5 C atoms or, respectively, 1, 2 or 3 C atoms, i.e. $C_{1-5}$-alkanyls, $C_{2-5}$-alkenyls and $C_{2-5}$-alkynyls or, respectively, $C_{1-3}$-alkanyls, $C_{2-3}$-alkenyls and $C_{2-3}$-alkynyls. Alkenyls here have at least one C—C double bond and alkynyls at least one C—C triple bond. Alkyl is advantageously chosen from the group which includes methyl, ethyl, n-propyl, 2-propyl, n-butyl, iso-butyl, sec-butyl, tert-butyl, n-pentyl, iso-pentyl, neo-pentyl, n-hexyl, 2-hexyl; ethylenyl (vinyl), ethynyl, propenyl (—$CH_2CH$=$CH_2$, —CH=CH—$CH_3$, —C(=$CH_2$)—$CH_3$), propynyl (—CH—C≡CH, —C≡C—$CH_3$), 1,1-dimethylethyl, 1,1-dimethylpropyl, butenyl, butynyl, pentenyl and pentynyl.

For the purposes of this invention, the expression "cycloalkyl" or "$C_{3-8}$-cycloalkyl" means cyclic hydrocarbons having 3, 4, 5, 6, 7 or 8 carbon atoms, wherein the hydrocarbons can be saturated or unsaturated (but not aromatic), unsubstituted or mono- or polysubstituted. With reference to cycloalkyl, the term also includes saturated or unsaturated (but not aromatic) cycloalkyls in which one or two carbon atoms are replaced by a heteroatom S, N or O. $C_{3-8}$-Cycloalkyl is advantageously chosen from the group which contains cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—.

In the context of this invention, the expression "aryl" means carbocyclic ring systems having at least one aromatic ring, but without heteroatoms in only one of the rings, inter alia phenyls, naphthyls and phenanthrenyls, fluoranthenyls, fluorenyls, indanyls and tetralinyls. The aryl radicals can also be fused with further saturated, (partly) unsaturated or aromatic ring systems. Each aryl radical can be unsubstituted or mono- or polysubstituted, wherein the substituents on the aryl can be identical or different and in any desired and possible position of the aryl. Phenyl or naphthyl radicals are particularly advantageous.

The expression "heteroaryl" represents a 5-, 6- or 7-membered cyclic aromatic radical which contains at least 1, optionally also 2, 3, 4 or 5 heteroatoms, wherein the heteroatoms are identical or different and the heterocyclic radical can be unsubstituted or mono- or polysubstituted; in the case of substitution on the heterocyclic radical, the substituents can be identical or different and in any desired and possible position of the heteroaryl. The heterocyclic radical can also be part of a bi- or polycyclic system. Preferred heteroatoms are nitrogen, oxygen and sulfur. It is preferable for the heteroaryl radical to be selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl and oxadiazolyl, wherein bonding to the compounds of the general structure I can take place via any desired and possible ring member of the heteroaryl radical.

In connection with "alkyl", in the context of this invention the term "substituted" is understood as meaning substitution of one or more hydrogen radicals by F, Cl, Br, I, —CN, $NH_2$, NH-alkyl, NH-aryl, NH-heteroaryl, NH-cycloalkyl, NH-alkyl-aryl, NH-alkyl-heteroaryl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, $C(=O)C_{1-16}$-alkyl, $C(=S)C_{1-6}$-alkyl, $C(=O)$aryl, $C(=S)$aryl, $C(=O)C_{1-6}$-alkyl-aryl, $C(=S)C_{1-6}$-alkyl-aryl, $C(=O)$-heteroaryl, $C(=S)$-heteroaryl, $C(=O)$-cycloalkyl, $C(=S)$-cycloalkyl, $CO_2H$, $CO_2$-alkyl, $CO_2$-alkyl-aryl, $C(=O)NH_2$, $C(=O)$NH-alkyl, $C(=O)$NHaryl, $C(=O)$NH-cycloalkyl, $C(=O)N(alkyl)_2$, $C(=O)N(alkyl-aryl)_2$, $C(=O)N(alkyl-heteroaryl)_2$, $C(=O)N(cycloalkyl)_2$, SO-alkyl, $SO_2$-alkyl, $SO_2NH_2$, $SO_3H$, $PO(O-C_{1-6}-alkyl)_2$, $Si(C_{1-6}-alkyl)_3$, $Si(C_{3-8}-cycloalkyl)_3$, $Si(CH_2-C_{3-8}-cycloalkyl)_3$, $Si(phenyl)_3$, cycloalkyl, aryl or heteroaryl, wherein polysubstituted radicals are to be understood as meaning those radicals which are poly-, e.g. di- or trisubstituted either on different or on the same atoms, for example trisubstituted on the same C atom as in the case of $CF_3$ or —$CH_2CF_3$, or at various places as in the case of —CH(OH)—CH=CH—$CHCl_2$. The polysubstitution can be by the same or by different substituents. A substituent can optionally also in its turn be substituted; thus, —Oalkyl also includes, inter alia, —O—$CH_2$—$CH_2$—O—$CH_2$—$CH_2$—OH.

In the context of this invention, with reference to "aryl", "heteroaryl" and "cycloalkyl", "mono- or polysubstituted" is understood as meaning mono- or poly-, e.g. di-, tri-tetra- or pentasubstitution of one or more hydrogen atoms of the ring system by F, Cl, Br, I, CN, $NH_2$, NH-alkyl, NH-aryl, NH-heteroaryl, NH-alkyl-aryl, NH-alkyl-heteroaryl, NH-cycloalkyl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, $NO_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, $C(=O)C_{1-6}$-alkyl, $C(=S)C_{1-6}$-alkyl, $C(=O)$aryl, $C(=S)$aryl, $C(=O)$—$C_{1-6}$-alkyl-aryl, $C(=S)C_{1-6}$-alkyl-aryl, $C(=O)$-heteroaryl, $C(=S)$-heteroaryl, $C(=O)$-cycloalkyl, $C(=S)$-cycloalkyl, $CO_2H$, $CO_2$-alkyl, $CO_2$-alkyl-aryl, $C(=O)NH_2$, $C(=O)$NH-alkyl, $C(=O)$NHaryl, $C(=O)$NH-cycloalkyl, $C(=O)N(alkyl)_2$, $C(=O)N(alkyl=aryl)_2$, $C(=O)N(alkyl-heteroaryl)_2$, $C(=O)N(cycloalkyl)_2$, S(O)-alkyl, S(O)-aryl, $SO_2$-alkyl, $SO_2$-aryl, $SO_2NH_2$, $SO_3H$, $CF_3$, =O, =S; alkyl, cycloalkyl, aryl and/or heteroaryl; on one or optionally different atoms (wherein a substituent can optionally in its turn be substituted). The polysubstitution here is by the same or by different substituents.

The term salt is to be understood as meaning any form of the active compound according to the invention in which this assumes an ionic form or is charged and is coupled with a counter-ion (a cation or anion) or is in solution. This is also to be understood as meaning complexes of the active compound with other molecules and ions, in particular complexes which are complexed via ionic interactions. In particular, by these there are understood (and this is also a preferred embodiment of this invention) physiologically acceptable salts, in particular physiologically acceptable salts with cations or bases and physiologically acceptable salts with anions or acids or also a salt formed with a physiologically acceptable acid or a physiologically acceptable cation.

In the context of this invention, the term physiologically acceptable salt with anions or acids is understood as meaning at least one of the compounds according to the invention— usually protonated, for example on the nitrogen—as the cation with at least one anion, which are physiologically acceptable—especially when used in humans and/or mammals. In particular, in the context of this invention by this there is understood the salt formed with a physiologically acceptable acid, namely salts of the particular active compound with inorganic or organic acids which are physiologically acceptable—especially when used in humans and/or mammals. Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, acetylsalicylic acid, hippuric acid and/or aspartic acid. The hydrochloride salt, the citrate and the hemicitrate are particularly preferred.

In the context of this invention, the term salt formed with a physiologically acceptable acid is understood as meaning salts of the particular active compound with inorganic or organic acids which are physiologically acceptable—especially when used in humans and/or mammals. The hydrochloride and the citrate are particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, acetylsalicylic acid, hippuric acid and/or aspartic acid.

In the context of this invention, the term physiologically acceptable salt with cations or bases is understood as meaning salts of at least one of the compounds according to the invention—usually of a (deprotonated) acid—as the anion with at least one preferably inorganic cation which are physiologically acceptable—especially when used in humans and/or mammals. The salts of the alkali metals and alkaline earth metals and also ammonium salts are particularly preferred, but especially (mono-) or (di-)sodium, (mono-) or (di-)potassium, magnesium or calcium salts.

In the context of this invention, the term salt formed with a physiologically acceptable cation is understood as meaning salts of at least one of the particular compounds as the anion with at least one inorganic cation which is physiologically acceptable—especially when used in humans and/or mammals. The salts of the alkali metals and alkaline earth metals and also ammonium salts are particularly preferred, but especially (mono-) or (di-)sodium, (mono-) or (di-)potassium, magnesium or calcium salts.

For a preferred embodiment of the spirocyclic cyclohexane derivatives according to the invention, $R^1$ and $R^2$ independently of one another represent H, $C_{1-5}$-alkyl, branched or unbranched, saturated or unsaturated, unsubstituted or mono- or polysubstituted, or CHO, $R^3$ represents phenyl, benzyl or phenethyl, in each case unsubstituted or mono- or polysubstituted on the ring $R^5$ represents H, $C_{1-5}$-alkyl, branched or unbranched, substituted or mono- or polysubstituted, $COOR^{13}$, $R^6$ represents H or $C_{1-5}$-alkyl, $R^7, R^8, R^9$ and $R^{10}$ independently of one another represent H; $C_{1-5}$-alkyl, branched or unbranched, unsubstituted or mono- or polysubstituted; F, Cl, Br, I, OH, $OCH_3$, $NH_2$, COOH, $COOCH_3$, $NHCH_3$, $N(CH_3)_2$, $NO_2$, $SO_3H$, $SO_2NH_2$, pyridyl or phenyl.

Compounds which are preferred according to the invention are also spirocyclic cyclohexane derivatives of the general formula I wherein W represents $NR^4$, O or S and X denotes O, S, SO, $SO_2$ or $NR^{17}$, $R^1$ and $R^2$ independently of one another represents H; $C_{1-4}$-alkyl, branched or unbranched, mono- or polysubstituted or unsubstituted; or CHO $R^3$ represents $(CH_2)_n$-aryl, in each case unsubstituted or mono- or polysubstituted on the aryl, where n=0-2, $R^4$ represents H; $C_{1-3}$-alkyl, mono- or polysubstituted or unsubstituted; $CO(CH_2)_mH$, where m=0 to 2, and/or $R^5$ and $R^6$ in each case represent H and/or $R^7, R^8, R^9$ and $R^{10}$ independently of one another represent H; $C_{1-5}$-alkyl, $OC_{1-3}$-alkyl, in each case branched or unbranched, saturated or unsaturated, unsubstituted or mono- or polysubstituted; F, Cl, Br, I, $CF_3$, OH, SH, $SCH_3$, $OCH_3$, $NH_2$, COOH, $COOCH_3$, $NHCH_3$, $N(CH_3)_2$, $NO_2$, $SO_3H$, $SO_2NH_2$, pyridyl or phenyl.

Compounds in which W represents $NR^4$ and X represents O, NH or $NCOR^{12}$ are particularly preferred.

For a particularly preferred embodiment of the spirocyclic cyclohexane derivatives according to the invention $R^1$ and $R^2$ independently of one another denote H or $CH_3$, with the proviso that $R^1$ and $R^2$ do not simultaneously denote H.

For a particularly preferred embodiment of the spirocyclic cyclohexane derivatives according to the invention, $R^3$ denotes phenyl, benzyl or phenethyl, in each case unsubstituted or mono- or polysubstituted on the ring. In particular, $R^3$ denotes phenyl, benzyl, phenethyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 3-trifluoromethylphenyl, 2-ethylphenyl, 3-ethylphenyl, 4-ethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert-butylphenyl, 4-fluoro-3-chlorophenyl, 4-bromo-3-fluorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl or 4-bromo-2-methylphenyl. Very particularly preferably, $R^3$ denotes phenyl, benzyl, phenethyl, 4-fluorophenyl or 3-fluorophenyl.

For a very particularly preferred embodiment of the spirocyclic cyclohexane derivatives according to the invention, the radical $R^5$ represents H, $CH_3$, COOH, $COOCH_3$ or $CH_2OH$, the radical $R^6$ represents H; $R^7, R^8, R^9$ and $R^{10}$ independently of one another denote H; $C_{1-5}$-alkyl, branched or unbranched, unsubstituted or mono- or polysubstituted; F, Cl, Br, I, $CF_3$, OH, $OCH_3$, $NH_2$, COOH, $COOCH_3$, $NHCH_3$, $N(CH_3)_2$, $NO_2$, $SO_3H$, $SO_2NH_2$, pyridyl or phenyl. Preferably the radicals $R^7, R^8, R^9$ and $R^{10}$ stand for H; or one of the radicals $R^7, R^8, R^9$ and $R^{10}$ represents H; $C_{1-5}$-alkyl, branched or unbranched, unsubstituted or mono- or polysubstituted, in particular methyl; and F, Cl, Br, I, OH, $OCH_3$, COOH, $COOCH_3$, $NH_2$, $NHCH_3$, $N(CH_3)_2$, $NO_2$, $SO_3H$, $SO_2NH_2$, pyridyl or phenyl, while the other radicals are H, wherein preferably one of the radicals $R^8$ or $R^9$ is other than H, or two of the radicals $R^7, R^8, R^9$ and $R^{10}$, preferably the radicals $R^8$ and $R^9$, independently of one another represent H; $C_{1-5}$-alkyl, branched or unbranched, unsubstituted or mono- or polysubstituted, in particular methyl; and F, Cl, Br, I, OH, $OCH_3$, COOH, $COOCH_3$, $NH_2$, $NHCH_3$, $N(CH_3)_2$, $NO_2$, $SO_3H$, $SO_2NH_2$, pyridyl or phenyl, while the other radicals are H.

Compounds in which W denotes $NR^4$, wherein $R^4$ represents H, $CH_3$, $C_2H_5$, acetyl, phenyl, benzyl or $COR^{12}$, and X denotes O, NH or $NCOR^{12}$ are furthermore particularly preferred.

For a very particularly preferred embodiment of the spirocyclic cyclohexane derivatives according to the invention $R^1$ and $R^2$ independently of one another denote H or $CH_3$, in particular $CH_3$, and $R^3$ denotes phenyl.

Very particularly preferred compounds include those selected from the group consisting of:

1,1-(3-dimethylamino-3-phenylpentamethylene)-1,3,4,9-tetrahydropyrano[3,4-b]indole hydrochloride 1,1-(3-dimethylamino-3-phenylpentamethylene)-1,3,4,9-tetrahydropyrano[3,4-b]indole hemicitrate 1,1-(3-dimethylamino-3-phenylpentamethylene)-1,3,4,9-tetrahydro-2-thia-9-azafluorene hemicitrate 1,1-(3-dimethylamino-3-phenylpentamethylene)-1,3,4,9-tetrahydro-2-thia-9-azafluorene citrate 1,1-(3-dimethylamino-3-phenylpentamethylene)-3,4-dihydro-1H-2-oxa-9-thiafluorene L-tartrate 1,1-(3-dimethylamino-3-(4-fluorophenyl)pentamethylene)-3,4-dihydro-1H-2-oxa-9-thiafluorene triflate 1,1-(3-dimethylamino-3-phenylpentamethylene)-3,4-dihydro-1H-2,9-dioxafluorene hemicitrate
1,1-(3-dimethylamino-3-phenylpentamethylene)-3,4-dihydro-1H-2,9-diazafluorene dihydrochloride
2-acetyl-1,1-(3-dimethylamino-3-phenylpentamethylene)-3,4-dihydro-1H-2,9-diazafluorene hydrochloride
1,1-(3-dimethylamino-3-phenylpentamethylene)-6-methoxy-1,3,4,9-tetrahydropyrano[3,4-b]indole hydrochloride
1,1-(3-dimethylamino-3-phenylpentamethylene)-3-methyl-1,3,4,9-tetrahydropyrano[3,4-b]indole citrate
6-bromo-1,1-(3-dimethylamino-3-phenylpentamethylene)-3-methyl-1,3,4,9-tetrahydropyrano[3,4-b]indole hemicitrate
1,1-(3-dimethylamino-3-phenylpentamethylene)-3-methyl-6-nitro-1,3,4,9-tetrahydropyrano[3,4-b]indole citrate
6-chloro-1,1-(3-dimethylamino-3-phenylpentamethylene)-3-methyl-1,3,4,9-tetrahydropyrano[3,4-b]indole citrate
3,9-dimethyl-1,1-(3-dimethylamino-3-phenylpentamethylene)-1,3,4,9-tetrahydropyrano[3,4-b]indole citrate
1,1-(3-dimethylamino-3-(4-fluorophenyl)pentamethylene)-1,3,4,9-tetra-hydro-pyrano[3,4-b]indole hemicitrate
1,1-(3-dimethylamino-3-(3-fluorophenyl)pentamethylene)-1,3,4,9-tetra-hydro-pyrano[3,4-b]indole hemicitrate
1,1-(3-dimethylamino-3-phenylpentamethylene)-6-fluoro-1,3,4,9-tetrahydropyrano[3,4-b]indole hemicitrate
1,1-(3-dimethylamino-3-phenylpentamethylene)-6-methyl-1,3,4,9-tetrahydropyrano[3,4-b]indole hemicitrate
1,1-(3-dimethylamino-3-phenylpentamethylene)-9-phenyl-1,3,4,9-tetrahydropyrano[3,4-b]indole citrate
1,1-(3-methylamino-3-phenyl(pentamethylene)-1,3,4,9-tetrahydro-pyrano-[3,4-b]indole hemicitrate
1,1-(3-dimethylamino-3-phenylpentamethylene)-6-methyl-3,4-dihydro-1H-2,9-diazafluorene citrate
2-acetyl-1,1-(3-dimethylamino-3-phenylpentamethylene)-6-methyl-3,4-dihydro-1H-2,9-diazafluorene citrate
1,1-(3-dimethylamino-3-phenylpentamethylene)-7-fluoro-3,4-dihydro-1H-2,9-diazafluorene citrate
2-acetyl-1,1-(3-dimethylamino-3-phenylpentamethylene)-7-fluoro-3,4-dihydro-1H-2,9-diazafluorene citrate
1,1-(3-dimethylamino-3-phenylpentamethylene)-3-methyl-3,4-dihydro-1H-2,9-diazafluorene citrate
1,1-(3-dimethylamino-3-phenylpentamethylene)-6-fluoro-3,4-dihydro-1H-2,9-diazafluorene dihydrochloride
1,1-(3-dimethylamino-3-phenylpentamethylene)-6-fluoro-3-methyl-1,3,4,9-tetrahydro-pyrano-[3,4-b]indole hemicitrate
3,6-dimethyl-1,1-(3-dimethylamino-3-phenylpentamethylene)-1,3,4,9-tetra-hydro-pyrano-[3,4-b]indole hemicitrate
3,6-dimethyl-1,1-(3-dimethylamino-3-phenylpentamethylene)-1,3,4,9-tetra-hydro-pyrano-[3,4-b]indole citrate
1,1-(3-dimethylamino-3-phenylpentamethylene)-3-methyl-9-phenyl-1,3,4,9-tetrahydropyrano[3,4-b]indole citrate
1,1-(3-dimethylamino-3-(4-fluorophenyl)pentamethylene)-1,3,4,9-tetra-hydro-2-thia-9-azafluorene methanesulfonate
1,1-(3-dimethylamino-3-(3-fluorophenyl)pentamethylene)-1,3,4,9-tetra-hydro-2-thia-9-azafluorene methanesulfonate
1,1-(3-dimethylamino-3-phenylpentamethylene)-3,4-dihydro-1H-9-oxa-2-thiafluorene citrate
1,1-(3-dimethylamino-3-phenylpentamethylene)-1,2,3,4-tetrahydro-benzo[4,5]furo[2,3-c]pyridine citrate
6,6-(3-dimethylamino-3-phenylpentamethylene)-1,2,3,4,4a,6,7,11c-octahydro-5-oxa-7-azabenzo[c]fluorene citrate
1,1-(3-dimethylamino-3-phenylpentamethylene)-6-bromo-1,3,4,9-tetrahydropyrano[3,4-b]indole hemicitrate
1,1-(3-dimethylamino-3-phenylpentamethylene)-1,3,4,9-tetrahydro-pyrano[3,4-b]indol-6-ol citrate
(3S)-1,1-(3-dimethylamino-3-phenylpentamethylene)-3,4-dihydro-3-methoxycarbonyl-1H-2,9-diazafluorene citrate
(3S)-1,1-(3-dimethylamino-3-phenylpentamethylene)-3,4-dihydro-1H-2,9-diazafluorene-3-methanol citrate
1,1-(3-dimethylamino-3-phenylethyl-pentamethylene)-3,4-dihydro-1H-2,9-diazafluorene
1,1-(3-methylamino-3-phenylpentamethylene)-6-fluoro-1,3,4,9-tetrahydropyrano[3,4-b]indole hemicitrate
1,1-(3-dimethylamino-3-(4-fluorophenyl)pentamethylene)-3,4-dihydro-1H-2,9-dithiafluorene methanesulfonate
1,1-(3-dimethylamino-3-phenylpentamethylene)-3,4-dihydro-1H-2,9-dithiafluorene citrate
1,1-(3-dimethylamino-3-phenylpentamethylene)-2-oxo-1,3,4,9-tetrahydro-2-thia-9-aza-fluorene citrate
1,1-(3-dimethylamino-3-benzylpentamethylene)-3,4-dihydro-1H-2,9-diazafluorene
and mixtures of two or more of the foregoing.

The substances according to the invention exhibit activity, for example, on the ORL1 receptor, which is relevant in connection with various diseases, so that they are suitable as a pharmaceutical active ingredient in a medicament. The invention therefore also relates to pharmaceutical compositions comprising at least one spirocyclic cyclohexane compound according to the invention and at least one suitable additive and/or auxiliary substance and/or optionally further active compounds.

In addition to at least one spirocyclic cyclohexane compound according to the invention, the pharmaceutical compositions according to the invention optionally comprise suitable additives and/or auxiliary substances, thus also carrier materials, fillers, solvents, diluents, dyestuffs and/or binders, and can be administered as liquid medicament forms in the form of injection solutions, drops or juices, or as semi-solid medicament forms in the form of granules, tablets, pellets, patches, capsules, plasters/spray plasters or aerosols. The choice of auxiliary substances etc. and the amounts thereof to be employed depend on whether the pharmaceutical composition is to be administered orally, perorally, parenterally, intravenously, intraperitoneally, intradermally, intramuscularly, intranasally, buccally, rectally or locally, for example to the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Spirocyclic cyclohexane derivatives according to the invention in a depot, in a dissolved form or in a plaster, optionally with the addition of agents which promote penetration through the skin, are suitable formulations for percutaneous administration. Formulation forms which can be used orally or percutaneously can release the spirocyclic cyclohexane derivatives according to the invention in a delayed manner. The spirocyclic cyclohexane derivatives according to the invention can also be used in parenteral long-term depot forms, such as e.g. implants or implanted pumps. In principle, other further active compounds known to the expert can be added to the medicaments according to the invention.

The amount of active compound to be administered to the patient varies according to the weight of the patient, the mode of administration, the indication and the severity of the disease. 0.00005 to 50 mg/kg, preferably 0.001 to 0.5 mg/kg of at least one spirocyclic cyclohexane derivative according to the invention are conventionally administered.

For the all the above forms of the pharmaceutical compositions according to the invention, it is particularly preferable if the medicament also comprises, in addition to at least one spirocyclic cyclohexane derivative, a further active compound, in particular an opioid, preferably a potent opioid, in particular morphine, or an anaesthetic, preferably hexobarbital or halothane.

In a preferred form of pharmaceutical composition, a spirocyclic cyclohexane compound according to the invention contained therein is in the form of a pure diastereomer and/or enantiomer, a racemate or a non-equimolar or equimolar mixture of the diastereomers and/or enantiomers.

As can be seen from the prior art in the introduction, the ORL1 receptor has been identified in particular in the pain event. Spirocyclic cyclohexane derivatives according to the invention can accordingly be used for the preparation of a pharmaceutical composition for treatment of pain, in particular acute, neuropathic or chronic pain. The invention therefore also relates to the use of a spirocyclic cyclohexane derivative according to the invention for the treatment of pain, in particular acute, visceral, neuropathic or chronic pain.

The invention also relates to the use of a spirocyclic cyclohexane compound according to the invention for the treatment of anxiety states, of stress and stress-associated syndromes, depressions, epilepsy, Alzheimer's disease, senile dementia, general cognitive dysfunctions, impaired learning and memory (as a nootropic), withdrawal symptoms, alcohol and/or drug and/or medicament abuse and/or dependency, sexual dysfunctions, cardiovascular diseases, hypotension, hypertension, tinitus, pruritus, migraine, impaired hearing, deficient intestinal motility, impaired food intake, anorexia, obesity, locomotor disorders, diarrhoea, cachexia, urinary incontinence or as a muscle relaxant, anticonvulsive or anaesthetic or for co-administration with an opioid analgesic or with an anaesthetic, for diuresis or antinatriuresis, anxiolysis, for modulation of motor activity, for modulation of neurotransmitter secretion and treatment of associated neurodegenerative diseases, for treatment of withdrawal symptoms and/or for reducing the addiction potential of opioids.

In one of the above uses, it may be preferable in this context if a spirocyclic cyclohexane derivative used is in the form of a pure diastereomer and/or enantiomer, a racemate or a non-equimolar or equimolar mixture of the diastereomers and/or enantiomers.

The invention also provides a method for treatment, in particular in one of the abovementioned indications, of a non-human mammal or human which or who requires treatment of pain, in particular chronic pain, by administration of a therapeutically active dose of a spirocyclic cyclohexane derivative according to the invention or of a medicament according to the invention.

The invention also provides a process for the preparation of the spirocyclic cyclohexane derivatives according to the invention as described in the following description and examples. A process which is particularly suitable in this context is a process, called the main process in the following, for the preparation of a spirocyclic cyclohexane derivative according to the invention with the following steps, wherein X, W, $R^1$, $R^2$, $R^3$, $R^5$, $R^6$, $R^7$, $R^8$, $R^9$ and $R^{10}$ have the meaning given for
compounds according to formula I according to the invention, and
$R^{01}$ and $R^{02}$ have the meaning given for $R^1$ and $R^2$ for compounds according to formula I according to the invention and additionally independently of one another can represent a protective group:

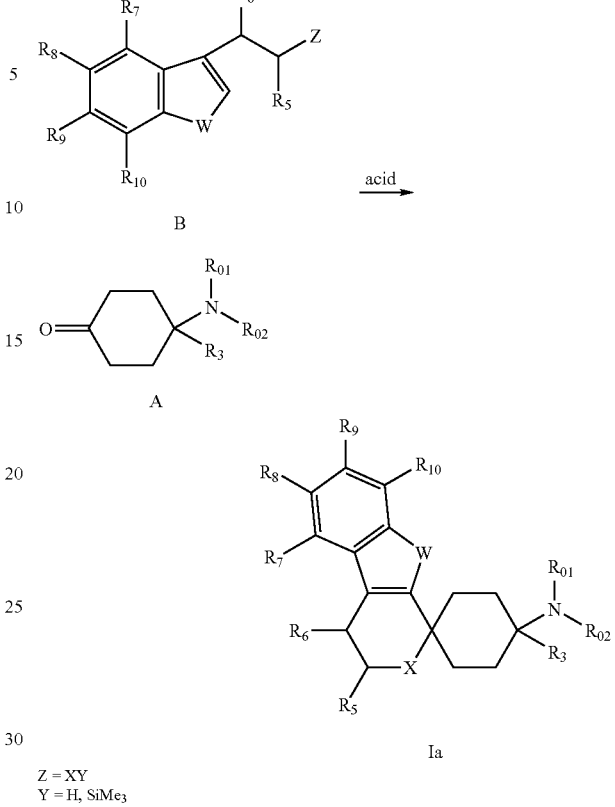

$Z = XY$
$Y = H, SiMe_3$

In order to prepare compounds corresponding to formula Ia, ketones of the general formula A are reacted with heteroaromatics of the general formula B, with the addition of acid or trimethylsilyl esters thereof, for example trifluoromethanesulfonic acid trimethylsilyl ester, acetic acid, phosphoric acid, methanesulfonic acid or trifluoroacetic acid, in a suitable solvent, for example dichloroethane, methylene chloride, chloroform, acetonitrile, diethyl ether or nitromethane. The preparation of the ketone intermediate A is carried out, in particular, in accordance with the following instructions:

a. a cyclohexane-1,4-dione according to formula II protected with the groups $S^1$ and $S^2$, which represent protective groups—for example substituted or unsubstituted alkyl, in particular $(CH_2)_n$, where n=2-4—is reacted with a cyanide, preferably potassium cyanide or TMSCN, in the presence of a compound of the formula $HNR^{01}R^{02}$, to give a protected N-substituted 1-amino-4-oxo-cyclohexanecarbonitrile derivative according to formula III;

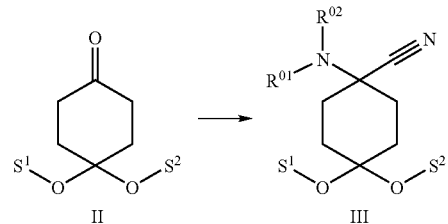

the product optionally subsequently, in any desired sequence and optionally repeatedly, is acylated, alkylated or sulfonated and/or in the case of compounds where $R^{01}$ and/or $R^{02}$=protective group a protective group is split off at least once, and the product optionally is acylated, alkylated or sulfonated and/or in the case of a compounds where $R^{01}$ and/or $R^{02}$=H a protective group is introduced at least once, and the product is optionally acylated, alkylated or sulfonated, b. the aminonitrile according to formula III is reacted with organometallic reagents, preferably Grignard or organolithium reagents, of the formula metal-$R^3$, so that a compound according to formula IV is formed;

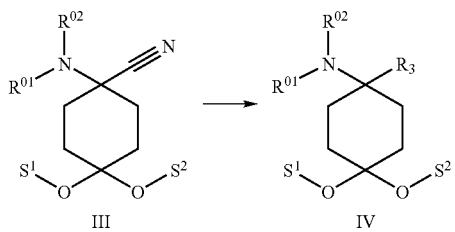

III → IV the product optionally subsequently, in any desired sequence and optionally repeatedly, is acylated, alkylated or sulfonated and/or in the case of compounds where $R^{01}$ and/or $R^{02}$=protective group a protective group is split off at least once, and the product optionally is acylated, alkylated or sulfonated and/or in the case of a compounds where $R^{01}$ and/or $R^{02}$=H a protective group is introduced at least once, and the product is optionally acylated, alkylated or sulfonated, c. the protective groups $S^1$ and $S^2$ on the compound according to formula IV are split off, so that a 4-substituted 4-aminocyclohexanone derivative according to formula A is formed;

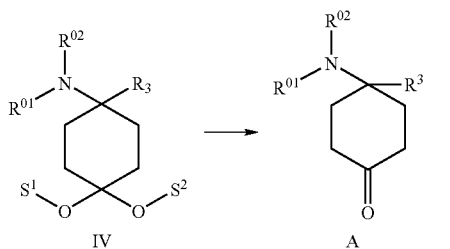

IV → A the product optionally subsequently, in any desired sequence and optionally repeatedly, is acylated, alkylated or sulfonated and/or in the case of compounds where $R^{01}$ and/or $R^{02}$=protective group a protective group is split off at least once, and the product optionally is acylated, alkylated or sulfonated and/or in the case of a compounds where $R^{01}$ and/or $R^{02}$=H a protective group is introduced at least once, and the product is optionally acylated, alkylated or sulfonated, wherein X, W, $R^3$, $R^5$, $R^6$, $R^7$, $R^8$, $R^9$ and $R^{10}$ have the meaning given for compounds according to formula I according to the invention, and $R^{01}$ and $R^{02}$ have the meaning given for $R^1$ and $R^2$ for compounds according to formula I according to the invention and additionally independently of one another can represent a protective group:

Alternatively, the preparation can also be carried out in accordance with the following equation, wherein X, W, $R^3$, $R^5$, $R^6$, $R^7$, $R^8$, $R^9$ and $R^{10}$ have the meaning given for compounds according to formula I according to the invention and $R^{01}$ and $R^{02}$ have the meaning given for $R^1$ and $R^2$ for compounds according to formula I according to the invention and additionally independently of one another can represent a protective group.

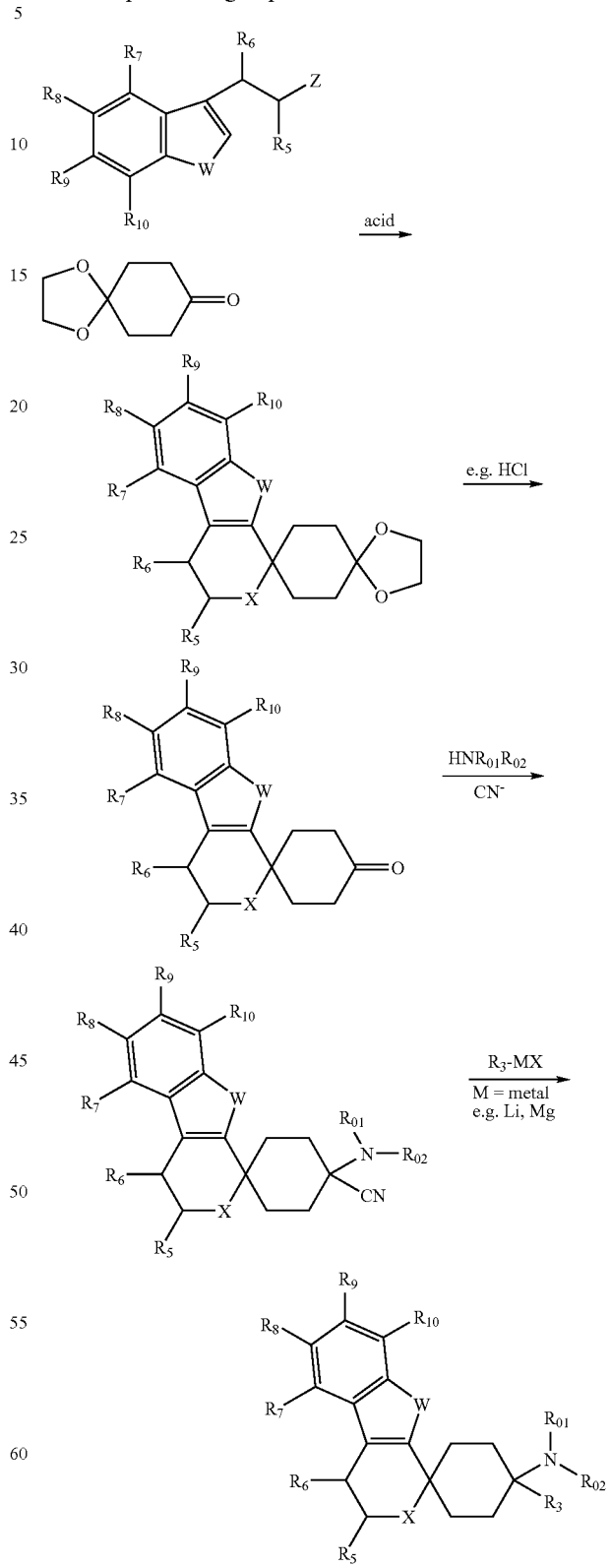

Z = XY
Y = H, SiMe₃

Spirocyclic cyclohexane compounds corresponding to formula I in which X denotes $NR^{17}$ and $R^{17}$ denotes $COR^{12}$ or $SO_2R^{12}$ can be obtained by reaction of spirocyclic cyclohexane compounds corresponding to formula I in which X denotes NH by reaction with an anhydride or an acid chloride with the addition of a base, for example triethylamine. This reaction preferably takes place under microwave irradiation.

Spirocyclic cyclohexane compounds corresponding to formula I in which X denote SO or $SO_2$ can be obtained by reaction of spirocyclic cyclohexane derivatives of the general formula I in which X denotes S with an oxidizing agent, for example $H_2O_2$.

Isolation of the compounds according to the invention by column chromatography with silica gel as the stationary phase and ethyl acetate, methanol, ethanol, mixtures of ethyl acetate and methanol or ethanol or mixtures of ethyl acetate and diethyl ether as the mobile phase leads to separation of the diastereoisomers of varying polarity. These have been characterized on the basis of their migration time during the separation as "most non-polar diastereoisomer" (shortest migration time) to "most polar diastereoisomer" (longest migration time).

EXAMPLES

The following examples serve to illustrate the invention in more detail, but do not limit the general inventive idea. The yields of the compounds prepared are not optimized. All temperatures are uncorrected.

The term "ether" means diethyl ether, "EA" ethyl acetate and "MC" methylene chloride. The term "equivalents" means equivalent substance amount, "m.p." melting point or melting range, "decomp." decomposition, "RT" room temperature, "abs." absolute (anhydrous), "rac." racemic, "conc." concentrated, "min" minutes, "h" hours, "d" days, "vol. %" percent by volume, "wt. %" percent by weight and "M" is a concentration stated in moles per liter.

Silica gel 60 (0.040-0.063 mm) from E. Merck, Darmstadt was employed as the stationary phase for the column chromatography. The thin layer chromatography analyses were carried out with HPTLC precoated plates, silica gel 60 F 254 from E. Merck, Darmstadt. The mixture ratios of mobile phases for chromatography analyses are always stated in volume/volume.

The compounds employed in the following procedures either were obtainable commercially or their preparation is known from the prior art or has been deduced from the prior art in a manner obvious to those skilled in the art of chemical synthesis. The following references are particularly relevant for this: Jirkovsky et al., J. Heterocycl. Chem., 12, 1975, 937-940; Campaigne et al., J. Heterocycl. Chem., 2, 1965, 231-235; Efange et al., J. Med. Chem., 41, 1998, 4486-4491; Ellingboe et al., J. Med. Chem., 35, 1992, 1176-1183; Pearson et al., Aust. J. Chem., 44, 1991, 907-917; Yokohama et al., Chem. Pharm. Bull., 40, 1992, 2391-2398; Beck et al., J. Chem. Soc. Perkin 1, 1992, 813-822; Shinada et al., Tetrahedron Lett., 39, 1996, 7099-7102; Garden et al., Tetrahedron, 58, 2002, 8399-8412; Lednicer et al., J. Med. Chem., 23, 1980, 424-430.

Example 1

1,1-(3-Dimethylamino-3-phenylpentamethylene)-1,3,4,9-tetrahydropyrano[3,4-b]indole Hydrochloride, More Non-Polar Diastereoisomer And Example 2

1,1-(3-Dimethylamino-3-phenylpentamethylene)-1,3,4,9-tetrahydropyrano[3,4-b]indole Hydrochloride, More Polar Diastereoisomer And Example 3

1,1-(3-Dimethylamino-3-phenylpentamethylene)-1,3,4,9-tetrahydropyrano[3,4-b]indole Hemicitrate, More Non-Polar diastereoisomer Method A:

Trifluoromethanesulfonic acid trimethylsilyl ester (1 ml, 5 mmoles) was added under argon to a solution of 4-dimethylamino-4-phenylcyclohexanone (1.1 g, 5.07 mmoles) and 3-(2-trimethylsilanyloxyethyl)-1H-indole (1.4 g, 6.01 mmoles) in MC (30 ml) at −78° C. in the course of 5 min, while stirring. The mixture was stirred at −78° C. for 1 hour. The mixture was then brought to room temperature over a period of 4 hours and stirred at room temperature for a further 10 hours. For working up, 1 M NaOH (30 ml) was added to the reaction mixture and the mixture was stirred for 30 min. The organic phase was separated, and the aqueous phase which remained was extracted with MC (2×30 ml). The combined organic phases were washed with 1 M NaOH (1×30 ml) and water (2×30 ml) and dried over sodium sulfate. After the solvent had been distilled off, a yellow solid was obtained, which was washed with EA. After recrystallization of the crude product which remained from toluene, the more non-polar isomer of 1,1-(3-dimethylamino-3-phenylpentamethylene)-1,3,4,9-tetrahydropyrano[3,4-b]indole, which had a melting point of 279-284° C., was isolated in a yield of 0.8 g. The mother liquor which remained and the EA wash solution were concentrated. By means of purification by column chromatography on silica gel, first with EA/ethanol (volume ratio 8:2) then with EA/ethanol (volume ratio 1:1), it was possible to separate off the more non-polar compound already isolated (150 mg) and a further more polar isomer. After recrystallization from toluene, the more polar product was obtained in a yield of 60 mg with a melting point of 230-235° C.

Method B:

Tryptophol (322 mg, 2.0 mmoles) and 4-dimethylamino-4-phenylcyclohexanone (435 mg, 2.0 mmoles) were dissolved under argon in a mixture of acetic acid (4 ml) and 85 percent strength by weight phosphoric acid (1 ml), while stirring and cooling with ice. The mixture was stirred overnight at RT. The solid formed was filtered off with suction and washed with methanol. Only the more polar of the two possible diastereoisomers was obtained as a white solid in a yield of 600 mg with a melting point of 280-284° C.

Method C:

4-Dimethylamino-4-phenylcyclohexanone (868 mg, 4 mmoles) and tryptophol (644 mg, 4 mmoles) were initially introduced into abs. MC (30 ml) under argon. Triethylamine (0.07 ml, 0.5 mmoles) was added to the solution. Trifluoromethanesulfonic acid trimethylsilyl ester (0.9 ml, 4.7 mmoles) was then added very rapidly. The mixture was stirred at RT for 20 h. For working up, 1 M NaOH (50 ml) was added to the reaction mixture and the mixture was stirred for 30 min. The organic phase was separated, and the aqueous phase which remained was extracted with MC (3×30 ml). The combined organic phases were washed with water (2×30 ml) and dried over sodium sulfate. Methanol (40 ml) was added to the largely solid residue obtained after the solvent had been distilled off, and the mixture was heated, and stirred for 15 hours. The suspended solid is the more non-polar diastereoisomer. The more polar diastereoisomer was in the methanolic solution. The more non-polar isomer was obtained in a yield of 1.20 g with a melting point of 278-282° C. Recrystallization from isopropanol gave cotton wool-like crystals which contained one equivalent of isopropanol. The melting point of the recrystallized product was 289-293° C.

Method D:

4-Dimethylamino-4-phenylcyclohexanone (434 mg, 2 mmoles) and tryptophol (322 mg, 4 mmoles) were initially introduced into abs. MC (20 ml) under argon. Trifluoromethanesulfonic acid trimethylsilyl ester (0.4 ml, 2.07 mmoles) was then added very rapidly. The mixture was stirred at RT for 18 h. For working up, 1 M NaOH (20 ml) was added to the reaction mixture and the mixture was stirred for 30 min. The organic phase was separated, and the aqueous phase which remained was extracted with MC (3×30 ml). The combined organic phases were washed with water (2×30 ml) and dried over sodium sulfate. Methanol (20 ml) was added to the largely solid residue obtained after the solvent had been distilled off, and the mixture was heated, and stirred for 15 hours. The suspended solid is the more non-polar diastereoisomer. The more polar product was in the methanolic solution. The more non-polar diastereoisomer was obtained in a yield of 571 mg with a melting point of 284-286° C.

Method E:

4-Dimethylamino-4-phenylcyclohexanone (651 mg, 3 mmoles) and 3-(2-trimethylsilanyloxyethyl)-1H-indole (699 mg, 3 mmoles) were dissolved in abs. MC (20 ml) under argon. Trifluoromethanesulfonic acid (0.28 ml, 3.16 mmoles) was then added very rapidly. The mixture was stirred at RT for 20 hours. For working up, 1 M NaOH (20 ml) was added to the reaction mixture and the mixture was stirred for 30 min. The organic phase was separated, and the aqueous phase which remained was extracted with MC (3×30 ml). The combined organic phases were washed with water (2×30 ml) and dried over sodium sulfate. The solid residue obtained after the solvent had been distilled off was the more non-polar diastereoisomer (800 mg).

Example 1

Hydrochloride of the More Non-Polar Diastereoisomer

For preparation of the hydrochloride, the more non-polar diastereoisomer of 1,1-(3-dimethylamino-3-phenylpentamethylene)-1,3,4,9-tetrahydropyrano[3,4-b]indole (500 mg, 1.38 mmoles) was dissolved in 2-butanone (40 ml), chlorotrimethylsilane (250 μl, 1.98 mmoles) was added and the mixture was stirred at RT for 3 hours. The resulting solid was filtered out with suction. It was possible to obtain the hydrochloride of the more non-polar diastereoisomer in this way in a yield of 420 mg as a white solid with a melting point of 278-280° C.

Investigations of cardiovascular tolerability were carried out for Example 1. It was found that compared with the two opioids fentanyl and sufentanil, which are employed clinically, the compound of Example 1 has advantages in respect of cardiovascular tolerability.

Example 2

Hydrochloride of the More Polar Diastereoisomer

Chlorotrimethylsilane (25 μl, 0.198 mmoles) was added to a solution of the more polar diastereoisomer of 1,1-(3-dimethylamino-3-phenylpentamethylene)-1,3,4,9-tetrahydropyrano[3,4-b]indole (50 mg, 0.138 mmoles) in 2-butanone (10 ml). After a reaction time of 2 hours, it was possible to isolate the precipitated hydrochloride of the more polar diastereoisomer in a yield of 36 mg with a melting point of 271-272° C.

Example 3

Hemicitrate of the More Non-Polar Diastereoisomer

For preparation of the hemicitrate, the more non-polar diastereoisomer of 1,1-(3-dimethylamino-3-phenylpentamethylene)-1,3,4,9-tetrahydropyrano[3,4-b]indole (1.2 g, 3.33 mmoles) was dissolved in hot ethanol (350 ml), and a similarly hot solution of citric acid (1.2 g, 6.25 mmoles) in ethanol (30 ml) was added. After cooling, the mixture was left at approx. 10° C. for 4 hours. The resulting solid was filtered out with suction. It was possible to obtain the hemicitrate in this way in a yield of 1.05 g as a white solid with a melting point of 259-265° C.

Example 4

1,1-(3-Dimethylamino-3-phenylpentamethylene)-1, 3,4,9-tetrahydro-2-thia-9-azafluorene Hemicitrate, More Non-Polar Diastereoisomer And Example 5

1,1-(3-Dimethylamino-3-phenylpentamethylene)-1, 3,4,9-tetrahydro-2-thia-9-azafluorene Citrate, More Polar Diastereoisomer Method A:

4-Dimethylamino-4-phenylcyclohexanone (326 mg, 1.5 mmoles) and 2-(1H-indol-3-yl)ethanethiol (266 mg, 1.5 mmoles) were initially introduced into abs. MC (10 ml) under argon. The methanesulfonic acid trimethylsilyl ester (254 μl, 1.65 mmoles) was then added. The mixture was stirred at RT for 4 days. For working up, the methanesulfonate which had precipitated out was filtered off with suction and washed with MC (3×0.5 ml). The methanesulfonate was obtained in a yield of 306 mg as a white solid with a melting point of 243-245° C.—The MC phase was worked up under alkaline conditions (1 M NaOH, 30 ml, vigorous stirring for 1 hour), the phases were separated, and the MC phase was concentrated. The residue was covered with a layer of abs. ethanol (10 ml), and the mixture was stirred under reflux for 30 min. After standing at room temperature for several hours, the precipitate was filtered out with suction, washed with ethanol (4×1 ml) and then dried. A mixture of the more non-polar and more polar diastereoisomer of 1,1-(3-dimethylamino-3-phenylpentamethylene)-1,3,4,9-tetrahydro-2-thia-9-azafluorene was obtained in a yield of 182 mg.

Method B:

4-Dimethylamino-4-phenylcyclohexanone (386.5 mg, 1.78 mmoles) and 2-(1H-indol-3-yl)ethanethiol (315 mg, 1.78 mmoles) were dissolved in glacial acetic acid (8 ml) under argon. The mixture was cooled to 4° C. and 85 percent strength by weight phosphoric acid (2 ml) was added dropwise. Thereafter, the mixture was stirred at room temperature for 20 hours. For working up, the suspension formed was cooled to 5° C., 1 M NaOH (60 ml) was added and the mixture was stirred at room temperature for 1 hour. After addition of MC (50 ml), the mixture was stirred at room temperature for 2 hours. The clear phases were separated. The aqueous phase was extracted with MC (3×10 ml). The combined organic phases were dried over sodium sulfate, and the MC was distilled off. One of the two diastereoisomers of 1,1-(3-dimethylamino-3-phenylpentamethylene)-1,3,4,9-tetrahydro-2-thia-9-azafluorene was obtained in this way as a white solid in a yield of 603 mg with a melting point of 236-238° C.

Example 4

Hemicitrate of the More Non-Polar Diastereoisomer

The diastereoisomer mixture obtained by Method A (172 mg, 0.457 mmoles) was dissolved in hot ethanol (130 ml), citric acid (88.6 mg, 0.461 mmoles) was added and the mixture was stirred at 65° C. for 10 min. After cooling to RT, the mixture was stirred for 20 h. The solid formed was filtered off with suction, washed with cold ethanol (2×0.5 ml) and then dried. 85 mg of the hemicitrate of the more non-polar diastereoisomer of 1,1-(3-dimethylamino-3-phenylpentamethylene)-1,3,4,9-tetrahydro-2-thia-9-azafluorene were obtained (m.p. 241-243° C.).

Example 5

Citrate of the More Polar Diastereoisomer

The ethanolic mother liquor obtained according to Example 4 was reduced to 25 ml of solution, 20 ml Et$_2$O were added and the mixture was stirred at RT for 1 h. The precipitate was filtered off with suction, washed with Et$_2$O (3×2 ml) and dried (62 mg, m.p. 165-169° C., diastereoisomer mixture). A white solid were obtained again from the mother liquor by addition of a further 50 ml diethyl ether. This was also filtered out with suction, washed with Et$_2$O (3×2 ml) and dried. 32 mg of the citrate of the more polar diastereoisomer of 1,1-(3-dimethylamino-3-phenylpenta-methylene)-1,3,4,9-tetrahydro-2-thia-9-azafluorene were obtained (m.p. 155-160° C.).

Example 6

1,1-(3-Dimethylamino-3-phenylpentamethylene)-3,4-dihydro-1H-2-oxa-9-thiafluorene L-tartrate Method A:

4-Dimethylamino-4-phenylcyclohexanone (217 mg, 1 mmole) and 2-(benzo[b]thiophen-3-yl)ethanol (178 mg, 1 mmole) were initially introduced into abs. MC (10 ml) under argon. Trifluoromethanesulfonic acid trimethylsilyl ester (245 µl, 1.1 mmoles) was then added. The mixture was stirred at room temperature for 24 hours. After this time, the reaction mixture was pale brown in color and clear. For working up, 10 g ice were added, and the aqueous phase was adjusted to pH 11 with 1 M NaOH. The phases were separated. The aqueous phase was extracted with MC (3×10 ml). The organic phases were combined, washed with water (2×3 ml), dried and concentrated. 1,1-(3-Dimethylamino-3-phenylpentamethylene)-3,4-dihydro-1H-2-oxa-9-thiafluorene was obtained from the residue, by extraction by stirring with ethanol (15 ml) at the boiling point, as a diastereoisomerically pure white solid in a yield of 322 mg with a melting point of 219-222° C.

Method B:

4-Dimethylamino-4-phenylcyclohexanone (231.4 mg, 1.06 mmoles) and 2-(benzo[b]thiophen-3-yl)ethanol (190 mg, 1.06 mmoles) were initially introduced into abs. MC (10 ml) under argon. Methanesulfonic acid (130 µl, 2 mmoles) was then added. The mixture was stirred at room temperature for 20 hours. After this time, the reaction mixture was pale brown in color and clear. For working up, 20 ml 1 M NaOH were added and the mixture was stirred at RT for 30 min. The phases were separated. The aqueous phase (pH 11) was extracted with MC (3×10 ml). The organic phases were combined, washed with water (4×10 ml), dried and concentrated. 1,1-(3-Dimethylamino-3-phenylpentamethylene)-3,4-dihydro-1H-2-oxa-9-thiafluorene was obtained from the residue, by extraction by stirring with ethanol (10 ml) at the boiling point, as a diastereoisomerically pure white solid in a yield of 340 mg with a melting point of 218-222° C. The same diastereoisomer was obtained as by Method A.

Example 6

L-Tartrate 1,1-(3-Dimethylamino-3-phenylpentamethylene)-3,4-dihydro-1H-2-oxa-9-thiafluorene (110 mg, 0.29 mmole) was dissolved in hot ethanol (50 ml), and a 0.1 M solution of L-tartaric acid (3.2 ml, 0.32 mmole) in ethanol was added. After cooling to room temperature, the mixture was stirred for 24 hours. After 24 hours, the solvent was concentrated to a residual volume of approx. 10 ml. The solid which had now precipitated out was filtered out with suction at room temperature, washed with ethanol (3×1 ml) and dried. The L-tartrate of 1,1-(3-dimethylamino-3-phenylpentamethylene)-3,4-dihydro-1H-2-oxa-9-thiafluorene was obtained in this way in a yield of 130 mg as a white solid with a melting point of 220-224° C.

Example 7

1,1-(3-Dimethylamino-3-(4-fluorophenyl)pentamethylene)-3,4-dihydro-1H-2-oxa-9-thiafluorene Triflate 4-Dimethylamino-4-(4-fluorophenyl)cyclohexanone (470.6 mg, 2 mmoles) and 2-(benzo[b]thiophen-3-yl)ethanol (356.5 mg, 2 mmoles) were initially introduced into abs. MC (20 ml) under argon. Trifluoromethane-sulfonic acid trimethylsilyl ester (0.425 ml, 2.2 mmoles) was then added. The mixture was stirred at RT for 64 h. For working up, the solid which had precipitated out was filtered out with suction, washed with MC (3×1 ml) and dried. The triflate of 1,1-(3-dimethylamino-3-(4-fluorophenyl)-pentamethylene)-3,4-dihydro-1H-2-oxa-9-thiafluorene was obtained in a yield of 383 mg as a diastereoisomerically pure white solid with a melting point of 212-215° C.

Example 8

1,1-(3-Dimethylamino-3-phenylpentamethylene)-3,4-dihydro-1H-2,9-dioxafluorene Hemicitrate 4-Dimethylamino-4-phenylcyclohexanone (868 mg, 4 mmoles) and 2-(benzofuran-3-yl)ethanol (648 mg, 4 mmoles) were initially introduced into abs. MC (20 ml) under argon. Trifluoromethanesulfonic acid trimethylsilyl ester (0.8 ml, 4.14 mmoles) was then added very rapidly. The mixture was stirred at room temperature for 2 hours. For working up, 1 M NaOH (20 ml) was added to the reaction mixture and the mixture was stirred for 30 min. The organic phase was separated, and the aqueous phase which remained was extracted with MC (3×20 ml). The combined organic phases were washed with water (2×30 ml) and dried over sodium sulfate. Methanol (30 ml) was added to the solid residue obtained after the solvent had been distilled off, and the mixture was heated, and stirred for 15 hours. The content which was insoluble in methanol was filtered out with suction. One of the two possible diastereoisomers of 1,1-(3-dimethylamino-3-phenylpentamethylene)-3,4-dihydro-1H-2,9-dioxafluorene was obtained in this manner in a yield of 650 mg with a melting point of 206-208° C. For preparation of the hemicitrate, the crude product obtained (600 mg, 1.66 mmoles) was dissolved in hot ethanol (100 ml), and a similarly hot solution of citric acid (600 mg, 3.12 mmoles) in ethanol (20 ml) was added. After cooling to approx. 5° C., a solid precipitated out and, after standing for 2 hours, was filtered out with suction. The hemicitrate of 1,1-(3-dimethyl-amino-3-phenylpentamethylene)-3,4-dihydro-1H-2,9-dioxafluorene was obtained in this way in a yield of 626 mg as a white solid (m.p.: 201-202° C.).

Example 9

1,1-(3-Dimethylamino-3-phenylpentamethylene)-3,4-dihydro-1H-2,9-diazafluorene Dihydrochloride, More Non-Polar Diastereoisomer 4-Dimethylamino-4-phenylcyclohexanone (1.09 g, 5 mmoles) and tryptamine (800 mg, 5 mmoles) were dissolved in dry 1,2-dichloroethane (50 ml) with exclusion of oxygen. Trifluoroacetic acid (770 µl, 10 mmoles) and sodium sulfate (2 g) were added to this mixture, while stirring. After a reaction time of 15 hours, trifluoroacetic acid (3 ml) was again added to the reaction mixture and the mixture was stirred at room temperature for a further 16 hours. For working up, the solvent was distilled off, and water (20 ml) was added to the residue. This aqueous phase was adjusted to pH 11 with NaOH (5 mol/l) and extracted with EA (3×30 ml). The organic phase was dried with sodium sulfate and concentrated. The product was a mixture of the two diastereoisomeric 1,1-(3-dimethylamino-3-phenylpentamethylene)-3,4-dihydro-1H-2,9-diazafluorenes, which it was possible to separate by chromatography on silica gel with methanol. The more non-polar product was obtained in a yield of 557 mg (31%) as a white solid. For preparation of the dihydrochloride, these 557 mg were suspended in 2-butanone (7 ml), and chlorotrimethylsilane (500 µl, 3.75 mmoles) was added. The resulting solid was filtered out with suction and dried. The dihydrochloride of the more non-polar diastereoisomer of 1,1-(3-dimethylamino-3-phenylpentamethylene)-3,4-dihydro-1H-2,9-diazafluorene was obtained in this way in a yield of 670 mg as a white solid with a melting point of 243-247° C.

Example 10

1,1-(3-Dimethylamino-3-phenylpentamethylene)-3,4-dihydro-1H-2,9-diazafluorene Dihydrochloride, More Polar Diastereoisomer As described for Example 9, 449 mg of the more polar diastereoisomer of 1,1-(3-dimethylamino-3-phenylpentamethylene)-3,4-dihydro-1H-2,9-diazafluorene were also obtained as a white solid. For preparation of the dihydrochloride, these 449 mg were suspended in 2-butanone (7 ml), and chlorotrimethylsilane (417 µl, 3.13 mmoles) was added. The solid thereby formed was filtered off with suction and dried. The dihydrochloride of the more polar diastereoisomer of 1,1-(3-dimethylamino-3-phenylpentamethylene)-3,4-dihydro-1H-2,9-diazafluorene was obtained in this way in a yield of 540 mg as a white solid with a melting point of 244-246° C.

Example 11

2-Acetyl-1,1-(3-dimethylamino-3-phenylpentamethylene)-3,4-dihydro-1H-2,9-diazafluorene Hydrochloride, More Non-Polar Diastereoisomer Method A:
The more non-polar diastereoisomer of 1,1-(3-dimethylamino-3-phenylpentamethylene)-3,4-dihydro-1H-2,9-diazafluorene (375 mg, 1.04 mmoles) was dissolved in pyridine (10 ml). Thereafter, acetic anhydride (985 µl, 10.43 mmoles) was added dropwise, and the mixture was stirred at room temperature for 2 days. For working up, pyridine was distilled off and water (10 ml) was added to the residue. The mixture was adjusted to pH 11 with 5 M NaOH and extracted with EA (3×15 ml). The organic phase was dried with sodium sulfate and evaporated. The residue was purified by column chromatography on silica gel with methanol. The acetamide of the more non-polar diastereoisomer of 1,1-(3-dimethylamino-3-phenylpentamethylene)-3,4-dihydro-1H-2,9-diazafluorene was obtained in this way in a yield of 356 mg as a white solid. For preparation of the hydrochloride, these 356 mg were suspended in 2-butanone (5 ml), and chlorotrimethylsilane (178 µl, 1.34 mmoles) was added. The resulting solid was filtered out with suction and dried. The hydrochloride of the more non-polar diastereoisomer of 2-acetyl-1,1-(3-dimethylamino-3-phenylpenta-methylene)-3,4-dihydro-1H-2,9-diazafluorene was obtained in this way in a yield of 388 mg as a white solid with a melting point of 220-223° C.

Method B:
Triethylamine (0.31 ml; 2.23 mmoles) and then acetic anhydride (0.21 ml; 2.23 mmoles) were added to a suspension of the more non-polar diastereoisomer of 1,1-(3-dimethylamino-3-phenylpentamethylene)-3,4-dihydro-1H-2,9-diazafluorene (80 mg; 0.22 mmole) in 15 ml acetonitrile. The reaction mixture was heated at 130° C. in a closed vessel in a microwave oven (MLS-Ethos 1600 from MLS GmbH, Leutkirch im Allgäu, Germany) for 10 minutes at 1,000 watt. 5 M aqueous potassium hydroxide solution (6 ml) and water (4 ml) were then added, and the aqueous phase was extracted with methylene chloride (3×10 ml). After the organic phase had been separated and dried with sodium sulfate and the solvent had been removed in vacuo, further purification was carried out by column chromatography on silica gel with EA and methanol. 49 mg of the acetylated base were obtained. It was possible to carry out precipitation of the hydrochloride as described under Method A.

Example 12

2-Acetyl-1,1-(3-dimethylamino-3-phenylpentamethylene)-3,4-dihydro-1H-2,9-diazafluorene Hydrochloride, More Polar Diastereoisomer The more polar diastereoisomer of 1,1-(3-dimethylamino-3-phenylpentamethylene)-3,4-dihydro-1H-2,9-diazafluorene (375 mg, 1.04 mmoles) was dissolved in pyridine (10 ml). Thereafter, acetic anhydride (985 μl, 10.43 mmoles) was added dropwise and the mixture was stirred at room temperature for 2 days. For working up, pyridine was distilled off and water H₂O (10 ml) was added to the residue. The mixture was adjusted to pH 11 with 5 M NaOH and extracted with EA (3×15 ml). The organic phase was dried with sodium sulfate and evaporated. The product was purified by column chromatography on silica gel with methanol. The acetamide of the more polar diastereoisomer of 1,1-(3-dimethylamino-3-phenylpentamethylene)-3,4-dihydro-1H-2,9-diazafluorene was obtained in this way in a yield of 339 mg as a white solid. For preparation of the hydrochloride, these 339 mg were suspended in 2-butanone (5 ml), and chlorotrimethylsilane (168 μl, 1.27 mmoles) was added. The resulting solid was filtered off with suction and dried. The hydrochloride of the more polar diastereoisomer of 2-acetyl-1,1-(3-dimethylamino-3-phenylpentamethylene)-3,4-dihydro-1H-2,9-diazafluorene was obtained in this way in a yield of 370 mg as a white solid with a melting point of 186-188° C.

Example 13

1,1-(3-Dimethylamino-3-phenylpentamethylene)-6-methoxy-1,3,4,9-tetrahydropyrano[3,4-b]indole Hydrochloride 4-Dimethylamino-4-phenylcyclohexanone (550 mg, 2.5 mmoles) and 5-methoxy-3-(2-trimethylsilanyloxy-ethyl)-1H-indole (789 mg, 3 mmoles) were initially introduced into abs. MC (30 ml) under argon. The solution was cooled to approx. 0° C. with the aid of an ice/sodium chloride mixture, and trifluoromethanesulfonic acid trimethylsilyl ester (0.5 ml, 2.5 mmoles) was added in the course of 5 min, while stirring. The mixture was cooled in the ice-bath for a further 3 hours, brought to room temperature in the course of approx. 1 hour and then stirred at room temperature for a further 10 hours. For working up, 1 M NaOH (30 ml) was added to the reaction mixture and the mixture was stirred for 30 min. The organic phase was separated, and the aqueous phase which remained was extracted with MC (2×30 ml). The combined organic phases were washed with water (2×30 ml) and dried over sodium sulfate. Methanol (70 ml) was added to the largely solid residue obtained after the solvent had been distilled off, the mixture was stirred for 2 hours, and the resulting suspension was filtered. 478 mg of one of the two possible diastereoisomers of 1,1-(3-dimethylamino-3-phenylpentamethylene)-6-methoxy-1,3,4,9-tetrahydropyrano[3,4-b]indole were obtained with a melting point of 244-246° C. 430 mg of this were dissolved in 2-butanone (25 ml), chlorotrimethylsilane (250 μl, 1.98 mmoles) was added, and the mixture was stirred at room temperature for 30 minutes. The resulting solid was filtered out with suction. The hydrochloride of 1,1-(3-dimethylamino-3-phenylpentamethylene)-6-methoxy-1,3,4,9-tetrahydropyrano[3,4-b]indole was obtained in this way in a yield of 396 mg as a white solid with a melting point of 279-280° C.

Example 14

1,1-(3-Dimethylamino-3-phenylpentamethylene)-3-methyl-1,3,4,9-tetrahydropyrano[3,4-b]indole Hemicitrate, More Non-Polar Diastereoisomer 4-Dimethylamino-4-phenylcyclohexanone (434 mg, 2 mmoles) and 3-(2-trimethylsilanyloxypropyl)-1H-indole (592 mg, 2.4 mmoles) were initially introduced into abs. MC (15 ml) under argon. The solution was cooled to approx. 0° C. with the aid of an ice/sodium chloride mixture, and trifluoromethanesulfonic acid trimethylsilyl ester (0.39 ml, 2 mmoles) was added in the course of 5 min, while stirring. The mixture was cooled in the ice-bath for a further 4 hours. After warming to room temperature, it was stirred for a further 20 hours. For working up, 1 M NaOH (20 ml) was added to the reaction mixture and the mixture was stirred for 30 min. The organic phase was separated, and the aqueous solution which remained was extracted with MC (2×30 ml). The combined organic phases were washed with water (2×30 ml) and dried over sodium sulfate. Methanol (70 ml) was added to the largely solid residue obtained after the solvent had been distilled off, and the mixture was stirred for 2 hours. A suspension was formed, from which the more non-polar diastereoisomer of 1,1-(3-dimethylamino-3-phenylpentamethylene)-3-methyl-1,3,4,9-tetrahydropyrano[3,4-b]indole, which is sparingly soluble in methanol, was obtained by filtration in a yield of 127 mg as a white solid with a melting point of 306-312° C. 94 mg of this were dissolved in hot ethanol (50 ml), and a similarly hot solution of citric acid (48 mg, 0.25 mmole) in ethanol (10 ml) was added. After cooling, the mixture was left to stand for 3 days. The resulting solid was filtered out with suction. It was possible to obtain the hemicitrate of the more non-polar diastereoisomer of 1,1-(3-dimethylamino-3-phenylpentamethylene)-3-methyl-1,3,4,9-tetrahydropyrano[3,4-b]indole in this way in a yield of 67 mg as a white solid (decomp. from 280° C.).

Example 15

1,1-(3-Dimethylamino-3-phenylpentamethylene)-3-methyl-1,3,4,9-tetrahydropyrano[3,4-b]indole Citrate, More Polar Diastereoisomer 4-Dimethylamino-4-phenylcyclohexanone (149 mg, 0.69 mmole) and 1-(1H-indol-3-yl)propan-2-ol (120 mg, 0.69 mmole) were dissolved in conc. acetic acid (4 ml). Phosphoric acid (1 ml, 85 wt. %) was slowly added dropwise to this mixture. After a reaction time of 5 min, a red solution was formed, from which a white solid precipitated out. The mixture was stirred at room temperature for 16 hours. For working up, the mixture was diluted with water (20 ml), adjusted to pH 11 with 5 M NaOH and extracted with MC (3×20 ml). The organic phase was dried with sodium sulfate and evaporated. The residue chiefly consisted of the more polar diastereoisomer, which it was possible to obtain in a yield of 260 mg as a white solid. For preparation of the citrate, these 260 mg, 0.69 mmole) were suspended in hot ethanol (20 ml), and a similarly hot solution of citric acid (133 mg, 0.69 mmole) in ethanol (5 ml) was added. The substance thereby dissolved completely and no longer precipitated out even on cooling to approx. 5° C. Ethanol was removed on a rotary evaporator, and it was possible to obtain the citrate of the more polar diastereoisomer of 1,1-(3-dimethylamino-3-phenylpentamethylene)-3-methyl-1,3,4,9-tetrahydropyrano[3,4-b]indole in this way in a yield of 392 mg as a white solid (m.p.: 160-165° C.).

Example 16

6-Bromo-1,1-(3-dimethylamino-3-phenylpentamethylene)-3-methyl-1,3,4,9-tetrahydropyrano[3,4-b]indole Hemicitrate 4-Dimethylamino-4-phenylcyclohexanone (651 mg, 3 mmoles) and 5-bromo-3-(2-trimethylsilanyloxypropyl)-1H-indole (975 mg, 3 mmoles) were initially introduced into abs.

MC (15 ml) under argon. The solution was cooled to approx. 0° C. with the aid of an ice/sodium chloride mixture, and trifluoromethanesulfonic acid trimethylsilyl ester (0.6 ml, 3.1 mmoles) was added in the course of 5 min, while stirring. The mixture was cooled in the ice-bath for a further 2 hours. After warming to room temperature, it was stirred for a further 20 hours. For working up, 1 M NaOH (30 ml) was added to the reaction mixture and the mixture was stirred for 30 min. The organic phase was separated, and the aqueous solution which remained was extracted with MC (2×30 ml). The combined organic extracts were washed with water (2×30 ml) and dried over sodium sulfate. Methanol (70 ml) was added to the largely solid residue obtained after the solvent had been distilled off, and the mixture was stirred for 1 hour. The material which had not dissolved was filtered out with suction. It proved to be one of the two possible racemic diastereoisomers of 6-bromo-1,1-(3-dimethylamino-3-phenylpentamethylene)-3-methyl-1,3,4,9-tetrahydropyrano[3,4-b]indole, which was obtained in this way in a yield of 260 mg (19%) as a white solid with a melting point of 287-293° C. in the pure form. 250 mg of this were dissolved in hot ethanol (120 ml), and a similarly hot solution of citric acid (120 mg, 0.62 mmole) in ethanol (10 ml) was added. The mixture was cooled and left at approx. 10° C. for 20 hours. The solid formed was filtered out with suction. It was possible to obtain the hemicitrate of 6-bromo-1,1-(3-dimethylamino-3-phenyl-pentamethylene)-3-methyl-1,3,4,9-tetrahydro-pyrano[3,4-b]indole in this way in a yield of 188 mg as a white solid (m.p. from 230° C. crystal conversion, from 290° C. sublimation).

Example 17

1,1-(3-Dimethylamino-3-phenylpentamethylene)-3-methyl-6-nitro-1,3,4,9-tetrahydropyrano[3,4-b]indole Citrate, More Non-Polar Diastereoisomer 4-Dimethylamino-4-phenylcyclohexanone (651 mg, 3 mmoles) and 5-nitro-3-(2-trimethylsilanyloxy-propyl)-1H-indole (876 mg, 3 mmoles) were initially introduced into abs. MC (20 ml) under argon. The solution was cooled to approx. 0° C. with the aid of an ice/sodium chloride mixture, and trifluoromethanesulfonic acid trimethylsilyl ester (0.6 ml, 3.1 mmoles) was added in the course of 5 min, while stirring. The mixture was cooled in the ice-bath for a further 2 h. After warming to RT, it was stirred for a further 70h. For working up, 1 M NaOH (50 ml) and MC (20 ml) were added to the reaction mixture and the mixture was stirred for 30 min. The organic phase was separated, and the aqueous solution which remained was extracted with MC (3×40 ml). The combined organic phases were washed with water (2×30 ml) and dried over sodium sulfate. Methanol (30 ml) was added to the vitreous residue obtained after the solvent had been distilled off, and the mixture was stirred for 1 h. The solid which was insoluble in methanol proved to be a diastereoisomer mixture. It was possible to separate the two racemic diastereoisomers by separation by column chromatography on silica gel (mobile phase: EA). The more non-polar product was obtained in a yield of 154 mg as a white solid with a melting point of 252-265° C. in the pure form. 134 mg of this were dissolved in hot ethanol (150 ml), and a similarly hot solution of citric acid (110 mg, 0.57 mmole) in ethanol (20 ml) was added. The mixture was cooled and left at approx. 10° C. for 20 h. The solid formed was filtered off with suction. The citrate of the more non-polar diastereoisomer of 1,1-(3-dimethylamino-3-phenylpentamethylene)-3-methyl-6-nitro-1,3,4,9-tetrahydropyrano[3,4-b]indole was obtained in this way in a yield of 117 mg with a melting point of 258-262° C.

Example 18

1,1-(3-Dimethylamino-3-phenylpentamethylene)-3-methyl-6-nitro-1,3,4,9-tetrahydropyrano[3,4-b]indole Citrate, More Polar Diastereoisomer As described for Example 17, 120 mg of the more polar diastereo-isomer of 1,1-(3-dimethylamino-3-phenylpentamethylene)-3-methyl-6-nitro-1,3,4,9-tetrahydropyrano[3,4-b]indole with a melting point of 230-240° C. were also obtained. These 120 mg were dissolved in hot ethanol (120 ml), and a similarly hot solution of citric acid (100 mg, 0.52 mmole) in ethanol (10 ml) was added. The solution was cooled and concentrated to dryness in vacuo. The residue obtained was taken up in water (10 ml), the citrate being obtained as a crystalline solid. After filtration and drying, the citrate of the more polar diastereoisomer of 1,1-(3-dimethylamino-3-phenylpenta-methylene)-3-methyl-6-nitro-1,3,4,9-tetrahydropyrano[3,4-b]indole was obtained in a yield of 76 mg with a melting point of 190-192° C.

Example 19

6-Chloro-1,1-(3-dimethylamino-3-phenylpentamethylene)-3-methyl-1,3,4,9-tetrahydropyrano[3,4-b]indole Citrate, More Non-Polar Diastereoisomer 4-Dimethylamino-4-phenylcyclohexanone (600 mg, 2.76 mmoles) and 5-chloro-3-(2-trimethylsilanyloxypropyl)-1H-indole (846 mg, 3 mmoles) were initially introduced into abs. MC (30 ml) under argon. The solution was cooled to approx. 0° C. with the aid of an ice/sodium chloride mixture, and trifluoromethanesulfonic acid trimethylsilyl ester (0.6 ml, 3.1 mmoles) was added in the course of 5 min, while stirring. The mixture was cooled in the ice-bath for a further 2 hours. After warming to room temperature, it was stirred for a further 18 hours. For working up, 1 M NaOH (30 ml) was added to the reaction mixture and the mixture was stirred for 30 min. The organic phase was separated, and the aqueous solution which remained was extracted with MC (2×30 ml). The combined organic phases were washed with water (2×30 ml) and dried over sodium sulfate. Methanol (50 ml) was added to the oily residue obtained after the solvent had been distilled off, and the mixture was stirred for 1 hour. A suspension was formed. The solid, which was insoluble in methanol, was separated, and it was possible to obtain the more non-polar diastereoisomer of 6-chloro-1,1-(3-dimethylamino-3-phenylpentamethylene)-3-methyl-1,3,4,9-tetrahydropyrano[3,4-b]indole, by separation by column chromatography on silica gel (mobile phase: EA), in a yield of 60 mg as a white solid (m.p.: from 180° C.). 55 mg of this were dissolved in hot ethanol (40 ml), and a similarly hot solution of citric acid (50 mg, 0.26 mmole) in ethanol (10 ml) was added. The solution was cooled, and concentrated to dryness in vacuo. The residue obtained was taken up in water (10 ml), the citrate of the more non-polar diastereoisomer of 6-chloro-1,1-(3-dimethylamino-3-phenylpenta-methylene)-3-methyl-1,3,4,9-tetrahydropyrano[3,4-b]indole being obtained as a crystalline solid. After filtration and drying, 36 mg with a melting point of 185-195° C. were obtained.

Example 20

6-Chloro-1,1-(3-dimethylamino-3-phenylpentamethylene)-3-methyl-1,3,4,9-tetrahydropyrano[3,4-b]indole Citrate, More Polar Diastereoisomer 4-Dimethylamino-4-phenylcyclohexanone (217 mg, 1 mmole) and 1-(5-chloro-1H-indol-3-yl)propan-2-ol (209 mg, 1 mmole) were dissolved in conc. acetic acid (4 ml). Phosphoric acid (1 ml, 85 wt. %) was slowly added dropwise to this mixture. After a reaction time of 60 min, a red solution formed. It was stirred at RT for 20 hours. For working up, the mixture was diluted with water (20 ml), brought to pH 11 with 5 M NaOH and extracted with MC (3×20 ml). The organic phase was dried with sodium sulfate and evaporated. The product consisted almost exclusively of the more polar diastereoisomer of 6-chloro-1,1-(3-dimethylamino-3-phenylpentamethylene)-3-methyl-1,3,4,9-tetrahydropyrano[3,4-b] indole (390 g of yellow solid). These 390 mg were suspended in hot ethanol (20 ml), and a similarly hot solution of citric acid (385 mg, 2 mmoles) in ethanol (10 ml) was added. On cooling to approx. 5° C., the citrate of the more polar diastereoisomer of 6-chloro-1,1-(3-dimethylamino-3-phenylpentamethylene)-3-methyl-1,3,4,9-tetrahydropyrano[3,4-b]indole precipitated out. It was filtered off with suction and dried (768 mg of yellow solid, m.p. 155-160° C.

Example 21

3,9-Dimethyl-1,1-(3-dimethylamino-3-phenylpentamethylene)-1,3,4,9-tetrahydropyrano[3,4-b]indole Citrate 4-Dimethylamino-4-phenylcyclohexanone (434 mg, 2 mmoles) and 1-methyl-3-(2-trimethylsilanyloxy-propyl)-1H-indole (622 mg, 2 mmoles) were initially introduced into abs. MC (20 ml) under argon, trifluoromethanesulfonic acid (0.18 ml, 2 mmoles) was added, while stirring, and the mixture was stirred for 20 hours. For working up, 1 M NaOH (20 ml) was added to the reaction mixture and the mixture was stirred for 30 min. The organic phase was separated, and the aqueous solution which remained was extracted with MC (2×30 ml). The combined organic phases were washed with water (2×30 ml) and dried over sodium sulfate. Methanol (50 ml) was added to the residue obtained after the solvent had been distilled off, and the mixture was stirred for 1 hours. The solid which was insoluble in methanol was separated and dried. One of the two possible diastereoisomers of 3,9-dimethyl-1,1-(3-dimethylamino-3-phenylpentamethylene)-1,3,4,9-tetrahydropyrano[3,4-b]indole was obtained in this manner (560 mg, m.p. 210-212° C.). 388 mg of this were dissolved in hot ethanol (50 ml), and a similarly hot solution of citric acid (384 mg, 2 mmoles) in ethanol (20 ml) was added. The solution was cooled and concentrated to dryness in vacuo. The residue obtained was taken up in water (20 ml), the citrate being obtained as a crystalline solid after trituration. To bring the precipitation to completion, the aqueous solution was left to stand overnight. After filtration and drying, 285 mg of the citrate of 3,9-dimethyl-1,1-(3-dimethylamino-3-phenylpentamethylene)-1,3,4,9-tetrahydropyrano[3,4-b]indole were obtained (m.p. 156-158° C.).

Example 22

1,1-(3-Dimethylamino-3-(4-fluorophenyl)pentamethylene)-1,3,4,9-tetrahydropyrano[3,4-b]indole Hemicitrate 4-Dimethylamino-4-(4-fluorophenyl)cyclohexanone (705 mg, 3 mmoles) and tryptophol (483 mg, 3 mmoles) were initially introduced into abs. MC (20 ml) under argon. Trifluoromethanesulfonic acid trimethylsilyl ester (0.6 ml, 3.1 mmoles) was then added very rapidly. The mixture was stirred at room temperature for 18 hours. For working up, 1 M NaOH (20 ml) was added to the reaction mixture and the mixture was stirred for 30 min. The organic phase was separated, and the aqueous phase which remained was extracted with MC (3×30 ml). The combined organic phases were washed with water (2×30 ml) and dried over sodium sulfate. Methanol (20 ml) was added to the solid residue obtained after the solvent had been distilled off, and the mixture was heated, and stirred for 15 hours. The solid contained in the suspension was filtered out with suction. One of the two possible diastereoisomers of 1,1-(3-dimethylamino-3-(4-fluorophenyl)pentamethylene)-1,3,4,9-tetrahydropyrano[3,4-b]indole was obtained in this manner (755 mg, m.p. 292-302° C.). These 755 mg were dissolved in hot ethanol (400 ml), and a similarly hot solution of citric acid (600 mg, 3.12 mmoles) in ethanol (50 ml) was added. After cooling to approx. 5° C., the mixture was left to stand for 2 hours. The resulting solid was filtered out with suction. The hemicitrate of 1,1-(3-dimethylamino-3-(4-fluorophenyl)pentamethylene)-1,3,4,9-tetrahydropyrano[3,4-b]indole was obtained (632 mg of white solid, m.p. 241-250° C. with decomposition).

Example 23

1,1-(3-Dimethylamino-3-(3-fluorophenyl)pentamethylene)-1,3,4,9-tetrahydropyrano[3,4-b]indole Hemicitrate 4-Dimethylamino-4-(3-fluorophenyl)cyclohexanone (434 mg, 1.84 mmoles) and tryptophol (296 mg, 1.84 mmoles) were initially introduced into abs. MC (20 ml) under argon. Trifluoromethanesulfonic acid trimethylsilyl ester (0.38 ml, 1.97 mmoles) was then added very rapidly. The mixture was stirred at room temperature for 20 hours. For working up, 1 M NaOH (20 ml) was added to the reaction mixture and the mixture was stirred for 30 min. The organic phase was separated, and the aqueous phase which remained was extracted with MC (3×100 ml). The combined organic phases were washed with water (2×30 ml) and dried over sodium sulfate. Methanol (20 ml) was added to the solid residue obtained after the solvent had been distilled off, and the mixture was heated, and stirred for 15 h. The solid contained in the suspension was filtered out with suction. One of the two possible diastereoisomers was obtained in this manner (482 mg, m.p. 298-301° C.). These 482 mg were dissolved in hot ethanol (400 ml), and a similarly hot solution of citric acid (490 mg, 2.55 mmoles) in ethanol (50 ml) was added. After cooling to approx. 5° C., the mixture was left to stand for 2 hours. The resulting solid was filtered out with suction. The hemicitrate of 1,1-(3-dimethylamino-3-(3-fluorophenyl)pentamethylene)-1,3,4,9-tetrahydropyrano[3,4-b]indole was obtained (351 mg of white solid, m.p. 286-291° C., from 245 crystal conversion, above 280° C. sublimation).

Example 24

1,1-(3-Dimethylamino-3-phenylpentamethylene)-6-fluoro-1,3,4,9-tetrahydropyrano[3,4-b]indole Hemicitrate, More Non-Polar Diastereoisomer 4-Dimethylamino-4-phenylcyclohexanone (651 mg, 3 mmoles) and 2-(5-fluoro-1H-indol-3-yl)-ethanol ("5-fluorotryptophol", 537 mg, 3 mmoles) were initially introduced into abs. MC (20 ml) under argon. Trifluoromethanesulfonic acid trimethylsilyl ester (0.6 ml, 3.1 mmoles) was then added very rapidly. The mixture was stirred at RT for 20 h. For working up, 1 M NaOH (30 ml) was added to the reaction mixture and the mixture was stirred for 30 min. The organic phase was separated, and the aqueous phase which remained was extracted with MC (3×60 ml). The combined organic phases were washed with water (2×30 ml) and dried over sodium sulfate. Methanol (30 ml) was added to the solid residue obtained after the solvent had been distilled off, and the mixture was heated, and stirred for 15 hours. The solid contained in the suspension was filtered off with suction and dried. 955 mg of the more non-polar diastereoisomer of 1,1-(3-dimethylamino-3-phenylpentamethylene)-6-fluoro-1,3,4, 9-tetrahydropyrano[3,4-b]indole were obtained (m.p. 284-292° C.). 850 mg of this were dissolved in hot ethanol (900 ml), and a similarly hot solution of citric acid (1 g, 5.2 mmoles) in ethanol (20 ml) was added. After approx. 15 minutes, crystals precipitated out at the boiling point. After cooling to approx. 5° C., the mixture was left to stand for 2 h. The solid formed was filtered off with suction. 640 mg of the hemicitrate were obtained as a white solid (m.p. 258-282° C.).

Example 25

1,1-(3-Dimethylamino-3-phenylpentamethylene)-6-fluoro-1,3,4,9-tetrahydropyrano[3,4-b]indole Hemicitrate, More Polar Diastereoisomer 4-Dimethylamino-4-phenylcyclohexanone (217 mg, 1 mmole) and 2-(5-fluoro-1H-indol-3-yl)-ethanol ("5-fluorotryptophol", 179 mg, 1 mmole) were dissolved in conc. acetic acid (4 ml). Phosphoric acid (1 ml, 85 wt. %) was slowly added dropwise to this mixture. The mixture was stirred at RT for 16 h. For working up, the mixture was diluted with water (20 ml), brought to pH 11 with 5 M NaOH and extracted with MC (3×20 ml). The combined organic phases were dried with sodium sulfate and evaporated. The residue (364 mg of white solid) was suspended in hot ethanol (20 ml), and a similarly hot solution of citric acid (185 mg, 0.96 mmole) in ethanol (5 ml) was added. The residue thereby dissolved completely and no longer precipitated out even on cooling to approx. 5° C. Ethanol was removed on a rotary evaporator and the hemicitrate of the more polar diastereoisomer of 1,1-(3-dimethylamino-3-phenylpentamethylene)-6-fluoro-1,3,4,9-tetrahydropyrano[3,4-b]indole was obtained in this way in a yield of 548 mg as a white solid (m.p. 148-155° C.).

Example 26

1,1-(3-Dimethylamino-3-phenylpentamethylene)-6-methyl-1,3,4,9-tetrahydropyrano[3,4-b]indole Hemicitrate 4-Dimethylamino-4-phenylcyclohexanone (325 mg, 1.5 mmoles) and 2-(5-methyl-1H-indol-3-yl)-ethanol ("5-methyltryptophol", 262 mg, 1.5 mmoles) were initially introduced into abs. MC (10 ml) under argon. Trifluoromethanesulfonic acid trimethylsilyl ester (0.3 ml, 1.55 mmoles) was then added very rapidly. The mixture was stirred at room temperature for 24 hours. For working up, 1 M NaOH (20 ml) was added to the reaction mixture and the mixture was stirred for 30 min. The organic phase was separated, and the aqueous phase which remained was extracted with MC (3×20 ml). The combined organic phases were washed with water (2×30 ml) and dried over sodium sulfate. Methanol (30 ml) was added to the solid residue obtained after the solvent had been distilled off, and the mixture was heated, and stirred for 15 hours. The suspended solid was filtered out with suction. One of the two possible diastereoisomers of 1,1-(3-dimethylamino-3-phenylpentamethylene)-6-methyl-1,3,4,9-tetrahydropyrano[3, 4-b]indole was obtained (430 mg, m.p. 259-270° C.). 350 mg of this were dissolved in hot ethanol (300 ml), and a similarly hot solution of citric acid (300 mg, 1.56 mmoles) in ethanol (10 ml) was added. After approx. 15 minutes, crystals precipitated out at the boiling point. After cooling to approx. 5° C., the mixture was left to stand for 2 hours. The resulting solid was filtered out with suction. It was possible to obtain the hemicitrate of 1,1-(3-dimethylamino-3-phenylpentamethylene)-6-methyl-1,3,4,9-tetrahydropyrano[3,4-b]indole in this way in a yield of 380 mg (white solid, m.p. 243-265° C.).

Example 27

1,1-(3-Dimethylamino-3-phenylpentamethylene)-9-phenyl-1,3,4,9-tetrahydropyrano[3,4-b]indole Citrate 4-Dimethylamino-4-phenylcyclohexanone (325 mg, 1.5 mmoles) and 2-(1-phenyl-1H-indol-3-yl)-ethanol (355 mg, 1.5 mmoles) were initially introduced into abs. MC (20 ml) under argon. Trifluoromethanesulfonic acid (0.14 ml, 1.58 mmoles) was then added very rapidly. The mixture was stirred at RT for 20 h. For working up, 1 M NaOH (30 ml) was added to the reaction mixture and the mixture was stirred for 30 min. The organic phase was separated, and the aqueous phase which remained was extracted with MC (3×60 ml). The combined organic phases were washed with water (2×30 ml) and dried over sodium sulfate. Methanol (30 ml) was added to the solid residue obtained after the solvent had been distilled off, and the mixture was heated, and stirred for 15 hours. The suspended solid was filtered out with suction. One of the two possible diastereoisomers of 1,1-(3-dimethylamino-3-phenylpentamethylene)-9-phenyl-1,3,4,9-tetrahydropyrano[3,4-b]indole was obtained (385 mg, m.p. 256-261° C.). 672 mg of this diastereoisomer of 1,1-(3-dimethylamino-3-phenyl-penta-methylene)-9-phenyl-1,3,4,9-tetrahydropyrano[3,4-b] indole were dissolved in hot ethanol (500 ml), and a similarly hot solution of citric acid (500 g, 2.6 mmoles) in ethanol (20 ml) was added. The solution was then concentrated to approx. 100 ml. After cooling to approx. 5° C., the mixture was left to stand for 48 hours. The resulting solid was filtered out with suction and dried. 570 mg of the citrate of 1,1-(3-dimethylamino-3-phenylpenta-methylene)-9-phenyl-1,3,4,9-tetrahydropyrano[3,4-b]indole were obtained (white solid, m.p. 255-260° C., from 205° C. crystal conversion).

Example 28

1,1-(3-Methylamino-3-phenylpentamethylene)-1,3,4, 9-tetrahydropyrano[3,4-b]indole Hemicitrate 4-Methylamino-4-phenyl-cyclohexanone (609 mg, 3 mmoles) and tryptophol (483 mg, 3 mmoles) were initially introduced into abs. MC (20 ml) under argon. Trifluoromethanesulfonic acid (0.28 ml, 3.16 mmoles) was then added very rapidly. The mixture was stirred at room temperature for 20 hours. For working up, 1 M NaOH (20 ml) was added to the reaction mixture, and the mixture was stirred for 30 min. The organic phase was separated, and the aqueous phase which remained was extracted with MC (3×30 ml). The combined organic extracts were washed with water (2×30 ml) and dried over sodium sulfate. Methanol (30 ml) was added to the solid residue obtained after the solvent had been distilled off, and the mixture was heated, and stirred for 15 hours. The solid contained in the suspension was filtered out with suction. One of the two possible diastereoisomers of 1,1-(3-methylamino-3-phenylpentamethylene)-1,3,4,9-tetrahydropyrano[3,4-b]indole was obtained in this manner in a yield of 630 mg (m.p. 260-262° C.). 600 mg of this were dissolved in hot ethanol (150 ml), and a similarly hot solution of citric acid (600 mg, 3.12 mmoles) in ethanol (10 ml) was added. After cooling to approx. 5° C., the mixture was left to stand for 12 hours. The resulting solid was filtered out with suction. 663 mg of the hemicitrate of 1,1-(3-methylamino-3-phenylpentamethylene)-1,3,4,9-tetrahydro-pyrano[3,4-b]indole were obtained (white solid, m.p. 252-254° C.).

Example 29

1,1-(3-Dimethylamino-3-phenylpentamethylene)-6-methyl-3,4-dihydro-1H-2,9-diazafluorene Citrate 4-Dimethylamino-4-phenylcyclohexanone (1.2 g, 5.53 mmoles) and 5-methyltryptamine (963 mg, 5.53 mmoles) were dissolved in dry methanol (40 ml) with exclusion of oxygen. Sodium sulfate (2 g) was added to this mixture. After a reaction time of 24 hours, the methanol was distilled off, and the residue was suspended in 1,2-dichloroethane (40 ml). Trifluoroacetic acid (4 ml) was added to the reaction mixture and the mixture was stirred at room temperature for 18 hours. For working up, the mixture was diluted with water (30 ml), adjusted to pH 11 with NaOH (5 mole/l) and extracted with 1,2-dichloroethane (3×30 ml). The organic phase was dried with sodium sulfate and concentrated. The brown solid residue was recrystallized from methanol. 236 mg of a white solid were obtained. 100 mg of this were dissolved in hot ethanol (10 ml), and a similarly hot solution of citric acid (62 mg, 0.32 mmole) in ethanol (1 ml) was added. After cooling to approx. 5° C., the mixture was left to stand for 4 hours. The resulting solid was filtered out with suction. The citrate of a diastereoisomer of 1,1-(3-dimethylamino-3-phenylpentamethylene)-6-methyl-3,4-dihydro-1H-2,9-diazafluorene was obtained in this way in a yield of 150 mg (as a white solid, m.p. 205-206° C.).

Example 30

2-Acetyl-1,1-(3-dimethylamino-3-phenylpentamethylene)-6-methyl-3,4-dihydro-1H-2,9-diazafluorene Citrate 120 mg (0.32 mmole) of the 1,1-(3-dimethylamino-3-phenylpenta-methylene)-6-methyl-3,4-dihydro-1H-2,9-diazafluorene prepared according to Example 29 were dissolved in pyridine (10 ml). Thereafter, acetic anhydride (305 µl, 3.2 mmoles) was added dropwise and the mixture was stirred at room temperature for 3 days. For working up, the pyridine was concentrated and the mixture was diluted with water (10 ml), brought to pH 11 with 5 M NaOH and extracted with EA (3×10 ml). The combined organic phases were dried with sodium sulfate and evaporated and the residue obtained was purified by column chromatography on silica gel with methanol. 120 mg of a white foam were obtained and were dissolved in hot ethanol (10 ml), and a similarly hot solution of citric acid (67 mg, 0.35 mmole) in ethanol (1 ml) was added. After cooling to approx. 5° C., the mixture was left to stand for 4 hours. The resulting solid was filtered out with suction. The citrate of 2-acetyl-1,1-(3-dimethylamino-3-phenyl-penta-methylene)-6-methyl-3,4-dihydro-1H-2,9-diazafluorene was obtained in a yield of 175 mg (white solid, m.p.: 162-167° C.).

Example 31

1,1-(3-Dimethylamino-3-phenylpentamethylene)-7-fluoro-3,4-dihydro-1H-2,9-diazafluorene Citrate, More Polar Diastereoisomer 4-Dimethylamino-4-phenylcyclohexanone (544 mg, 2.5 mmoles) and 6-fluorotryptamine (445 mg, 2.5 mmoles) were dissolved in dry methanol (20 ml). Sodium sulfate (1 g) was added to this mixture. After a reaction time of 24 hours, methanol was distilled off and the residue was suspended in 1,2-dichloroethane (20 ml). Trifluoroacetic acid (2 ml) was added to the reaction mixture and the mixture was stirred at room temperature for 18 hours. For working up, the mixture was diluted with water (20 ml), brought to pH 11 with NaOH (5 mole/l) and extracted with 1,2-dichloroethane (3×20 ml). The combined organic phases were dried with sodium sulfate and concentrated. The solid, white residue was recrystallized from methanol, and the more polar diastereoisomer (300 mg of white solid) was obtained from the mother liquor. These 300 mg were dissolved in hot ethanol (20 ml), and a similarly hot solution of citric acid (193 mg, 1 mmole) in ethanol (2 ml) was added. After cooling to approx. 5° C., the mixture was left to stand for 4 hours. The resulting solid was filtered out with suction and dried. The citrate of 1,1-(3-dimethylamino-3-phenylpentamethylene)-7-fluoro-3,4-dihydro-1H-2,9-diazafluorene was obtained in this way in a yield of 430 mg (white solid, m.p.: 224-226° C.).

Example 32

2-Acetyl-1,1-(3-dimethylamino-3-phenylpentamethylene)-7-fluoro-3,4-dihydro-1H-2,9-diazafluorene Citrate, More Non-Polar Diastereoisomer The residue obtained according to Example 31 by recrystallization from methanol was recrystallized again from EA. 330 mg of the more non-polar diastereoisomer of 1,1-(3-dimethylamino-3-phenylpentamethylene)-7-fluoro-3,4-dihydro-1H-2,9-diazafluorene were obtained as a white solid. 150 mg of this were dissolved in pyridine (10 ml). Thereafter, acetic anhydride (380 µl, 4 mmoles) was added dropwise and the mixture was stirred at RT for 3 days. For working up, the mixture was concentrated, diluted with water (10 ml), adjusted to pH 11 with 5 M NaOH and extracted with EA (3×10 ml). The combined organic phases were dried with sodium sulfate and evaporated. The resulting residue was purified by column chromatography on silica gel with methanol. The 154 mg 2-acetyl-1,1-(3-dimethylamino-3-phenylpentamethylene)-7-fluoro-3,4-dihydro-1H-2,9-diazafluorene obtained were dissolved in hot ethanol (10 ml), and a similarly hot solution of citric acid (87 mg, 0.45 mmole) in ethanol (1 ml) was added. After cooling to approx. 5° C., the mixture was left to stand for 4 hours. The resulting solid was filtered out with suction. The citrate of the more non-polar diastereoisomer of 2-acetyl-1,1-(3-dimethylamino-3-phenylpentamethylene)-7-fluoro-3,4-dihydro-1H-2,9-diazafluorene was obtained in this way in a yield of 230 mg (white solid, m.p. 135-140° C.).

Example 33

1,1-(3-Dimethylamino-3-phenylpentamethylene)-3-methyl-3,4-dihydro-1H-2,9-diazafluorene Citrate 4-Dimethylamino-4-phenylcyclohexanone (435 mg, 2 mmoles) and rac. 2-(1H-indol-3-yl)-1-methylethylamine ("DL-α-methyltryptamine", 348 mg, 2 mmoles) were dissolved in dry methanol (20 ml). Sodium sulfate (1 g) was added to this mixture. After a reaction time of 24 hours, methanol was distilled off, and the residue was suspended in 1,2-dichloroethane (20 ml). Trifluoroacetic acid (2 ml) was added to the reaction mixture and the mixture was stirred at room temperature for 16 hours. For working up, the mixture was diluted with water (20 ml), adjusted to pH 11 with NaOH (5 mole/l) and extracted with 1,2-dichloroethane (3×20 ml). The organic phase was dried with sodium sulfate and concentrated. The residue was a contaminated mixture of the two diastereoisomeric 1,1-(3-dimethylamino-3-phenylpentamethylene)-3-methyl-3,4-dihydro-1H-2,9-diazafluorenes, which it was possible to purify by recrystallization from methanol but not to separate (660 mg of white solid). 200 mg of this were dissolved in hot ethanol (15 ml), and a similarly hot solution of citric acid (124 mg, 0.64 mmole) in ethanol (2 ml) was added. After cooling to approx. 5° C., the mixture was left to stand for 3 hours. The resulting solid was filtered out with suction and dried. The citrate of 1,1-(3-dimethylamino-3-phenyl-pentamethylene)-3-methyl-3,4-dihydro-1H-2,9-diazafluorene was obtained in this way in a yield of 140 mg (white solid, m.p. 209-212° C.). Only one of the two diastereoisomers was obtained in this citrate precipitation.

Example 34

1,1-(3-Dimethylamino-3-phenylpentamethylene)-6-fluoro-3,4-dihydro-1H-2,9-diazafluorene Dihydrochloride 4-Dimethylamino-4-phenylcyclohexanone (1.01 g, 4.64 mmoles) and 5-fluorotryptamine (827 mg, 4.64 mmoles) were dissolved in dry methanol (40 ml). Sodium sulfate (2 g) was added to this mixture. After a reaction time of 24 hours, methanol was distilled off and the residue was suspended in 1,2-dichloroethane (40 ml). Trifluoroacetic acid (4 ml) was added to the reaction mixture, and the mixture was stirred at room temperature for 16 hours. For working up, the mixture was diluted with water (40 ml), adjusted to pH 11 with NaOH (5 mole/l) and extracted with 1,2-dichloroethane (3×25 ml). The combined organic phases were dried with sodium sulfate and concentrated. The brown solid residue obtained was recrystallized from methanol, the mixture of more polar and more non-polar diastereoisomer of 1,1-(3-dimethylamino-3-phenylpentamethylene)-6-fluoro-3,4-dihydro-1H-2,9-diazafluorene obtained (110 mg of white solid) was dissolved in 2-butanone (3 ml), and chlorotrimethylsilane (97 μl, 0.73 mmole) was added. The resulting solid was filtered out with suction and dried. The dihydrochloride of 1,1-(3-dimethylamino-3-phenylpentamethyl-ene)-6-fluoro-3,4-dihydro-1H-2,9-diazafluorene obtained (131 mg of white solid, m.p. 228-232° C.) was a 60:40 mixture of the two diastereoisomers.

Example 35

1,1-(3-Dimethylamino-3-phenylpentamethylene)-6-fluoro-3-methyl-1,3,4,9-tetrahydropyrano[3,4-b]indole Hemicitrate 4-Dimethylamino-4-phenylcyclohexanone (651 mg, 3 mmoles) and 1-(5-fluoro-1H-indol-3-yl)-propan-2-ol (579 mg, 3 mmoles) were initially introduced into abs. MC (20 ml) under argon. Trifluoromethanesulfonic acid trimethylsilyl ester (0.6 ml, 3.1 mmoles) was then added very rapidly. The mixture was stirred at room temperature for 20 hours. For working up, 1 M NaOH (20 ml) was added to the reaction mixture and the mixture was stirred for 30 min. The organic phase was separated, and the aqueous phase which remained was extracted with MC (3×30 ml). The combined organic phases were washed with water (2×30 ml) and dried over sodium sulfate. Methanol (25 ml) was added to the solid residue obtained after the solvent had been distilled off, and the mixture was heated, and stirred for 15 h. The solid which was insoluble in methanol was filtered out with suction. One of the two diastereoisomers of 1,1-(3-dimethylamino-3-phenylpentamethylene)-6-fluoro-3-methyl-1,3,4,9-tetrahydropyrano[3,4-b]indole was obtained in this manner in a yield of 856 mg (m.p. 232-236° C.). 800 mg of this were dissolved in hot ethanol (200 ml), and a similarly hot solution of citric acid (600 mg, 3.12 mmoles) in ethanol (20 ml) was added. After cooling to approx. 5° C., no crystal formation was to be observed. The solution was concentrated in vacuo. Water (30 ml) was added to the residue. After trituration, a precipitate precipitated out and, after complete crystallization, was filtered off with suction (hemicitrate of 1,1-(3-dimethylamino-3-phenylpentamethylene)-6-fluoro-3-methyl-1,3,4,9-tetrahydropyrano[3,4-b]indole, 807 mg of white solid, m.p. 180-182° C.).

Example 36

3,6-Dimethyl-1,1-(3-dimethylamino-3-phenylpentamethylene)-1,3,4,9-tetrahydropyrano[3,4-b]indole Hemicitrate, More Non-Polar Diastereoisomer 4-Dimethylamino-4-phenylcyclohexanone (651 mg, 3 mmoles) and 1-(5-methyl-1H-indol-3-yl)-propan-2-ol (567 mg, 3 mmoles) were initially introduced into abs. MC (20 ml) under argon. Trifluoromethanesulfonic acid trimethylsilyl ester (0.6 ml, 3.1 mmoles) was then added very rapidly. The mixture was stirred at RT for 20 h. For working up, 1 M NaOH (30 ml) was added to the reaction mixture and the mixture was stirred for 30 min. The organic phase was separated, and the aqueous phase which remained was extracted with MC (3×30 ml). The combined organic phases were washed with water (2×30 ml) and dried over sodium sulfate. Methanol (30 ml) was added to the solid residue obtained after the solvent had been distilled off, and the mixture was heated, and stirred for 15 hours. The more non-polar of the two possible racemic diastereoisomers of 3,6-dimethyl-1,1-(3-dimethylamino-3-phenylpentamethylene)-1,3,4,9-tetrahydropyrano[3,4-b]indole (840 mg, m.p. 292-296° C.) was obtained by filtering out the solid which was insoluble in methanol. 600 mg of this were dissolved in hot ethanol (300 ml), and a similarly hot solution of citric acid (400 mg, 2.08 mmoles) in ethanol (20 ml) was added. A solid already started to precipitate out at the boiling point. To bring the crystallization to completion, the solution was left at approx. 5° C. for 15 hours. The precipitate was then separated and dried. It was possible to obtain the hemicitrate of the more non-polar diastereoisomer of 3,6-dimethyl-1,1-(3-dimethylamino-3-phenylpentamethylene)-1,3,4,9-tetrahydropyrano[3,4-b]indole in this way in a yield of 630 mg (white solid, m.p. 258-276° C.).

Example 37

3,6-Dimethyl-1,1-(3-dimethylamino-3-phenylpentamethylene)-1,3,4,9-tetrahydropyrano[3,4-b]indole Citrate, More Polar Diastereoisomer 4-Dimethylamino-4-phenylcyclohexanone (217 mg, 1 mmole) and 1-(5-methyl-1H-indol-3-yl)-propan-2-ol (189 mg, 1 mmole) were dissolved in conc. acetic acid (4 ml). Phosphoric acid (1 ml, 85 wt. %) was slowly added dropwise to this mixture. After a reaction time of 60 min, a red solution formed. It was stirred at room temperature for 20 hours. For working up, the mixture was diluted with water (20 ml), adjusted to pH 11 with 5 M NaOH and extracted with MC (3×20 ml). The organic phase was dried with sodium sulfate and evaporated to dryness. The residue (370 mg of white solid) was suspended in hot ethanol (20 ml), and a similarly hot solution of citric acid (385 mg, 2 mmoles) in ethanol (10 ml) was added. The residue thereby dissolved completely, but precipitated out again on cooling to approx. 5° C. The citrate of the more polar diastereoisomer of 3,6-dimethyl-1,1-(3-dimethylamino-3-phenylpentamethylene)-1,3,4,9-tetrahydropyrano[3,4-b]indole was filtered out with suction and dried (690 mg of white solid, m.p. 162-168° C.).

Example 38

1,1-(3-Dimethylamino-3-phenylpentamethylene)-3-methyl-9-phenyl-1,3,4,9-tetrahydropyrano[3,4-b]indole Citrate 4-Dimethylamino-4-phenylcyclohexanone (435 mg, 2 mmoles) and 2-(1-phenyl-1H-indol-3-yl)-ethanol (503 mg, 2 mmoles) were dissolved in conc. acetic acid (8 ml). Phosphoric acid (2 ml, 85 wt. %) was slowly added dropwise to this mixture. After a reaction time of 30 min, a red solution formed. It was stirred at room temperature for 20 hours. For working up, the mixture was diluted with water (40 ml), brought to pH 11 with 5 M NaOH and extracted with MC (3×30 ml). The organic phase was dried with sodium sulfate and evaporated to dryness. The residue contained only one of the two possible racemic diastereoisomers of the target product, which it was possible to obtain in a yield of 900 mg as a white solid. These 900 mg were suspended in hot ethanol (50 ml), and a similarly hot solution of citric acid (770 mg, 4 mmoles) in ethanol (15 ml) was added. The solid which had precipitated out on cooling to approx. 5° C. was filtered out with suction and dried. It was possible to obtain the citrate of 1,1-(3-dimethylamino-3-phenylpentamethylene)-3-methyl-9-phenyl-1,3,4,9-tetrahydropyrano[3,4-b]indole in this way in a yield of 1.2 g as a white solid (m.p. 253-256° C.).

Example 39

1,1-(3-Dimethylamino-3-(4-fluorophenyl)pentamethylene)-1,3,4,9-tetrahydro-2-thia-9-azafluorene Methanesulfonate 4-Dimethylamino-4-(4-fluorophenyl)cyclohexanone (353 mg, 1.5 mmoles) and 2-(1H-indol-3-yl)ethanethiol (266 mg, 1.5 mmoles) were initially introduced into abs. MC (10 ml) under argon. Methanesulfonic acid trimethylsilyl ester (254 µl, 1.65 mmoles) was then added. After the mixture had been stirred at room temperature for 20 hours, no precipitate was visible. Methanesulfonic acid trimethylsilyl ester (254 µl, 1.65 mmole) was again added to the reaction mixture. Thereafter, the mixture was stirred for 3 days at room temperature. For working up, the methane-sulfonate which had precipitated out was filtered out with suction and washed with MC (3×1 ml) and diethyl ether (3×3 ml). The methane-sulfonate of one of the two possible diastereoisomers of 1,1-(3-dimethyl-amino-3-(4-fluorophenyl)penta-methylene)-1,3,4,9-tetrahydro-2-thia-9-aza-fluorene was obtained in a yield of 550 mg as a white solid (m.p. 245-250° C.).

Example 40

1,1-(3-Dimethylamino-3-(3-fluorophenyl)pentamethylene)-1,3,4,9-tetrahydro-2-thia-9-azafluorene Methanesulfonate 4-Dimethylamino-4-(3-fluorophenyl)cyclohexanone (353 mg, 1.5 mmoles) and 2-(1H-indol-3-yl)ethanethiol (266 mg, 1.5 mmoles) were initially introduced into abs. MC (10 ml) under argon. Methanesulfonic acid (195 µl, 3 mmoles) was then added. After the reaction mixture had been stirred at room temperature for 2 hours, it was a clear solution. After stirring at room temperature for a further 16 hours, a copious white precipitate had precipitated out. The suspension was diluted with MC (5 ml). The precipitate was filtered out with suction, washed with MC (3×1 ml) and dried. The methanesulfonate of one of the two possible diastereoisomers of 1,1-(3-dimethylamino-3-(3-fluorophenyl)penta-methylene)-1,3,4,9-tetrahydro-2-thia-9-azafluorene was obtained as a cream-colored solid (695 mg, m.p. 258-260° C.).

Example 41

1,1-(3-Dimethylamino-3-phenylpentamethylene)-3,4-dihydro-1H-9-oxa-2-thiafluorene Citrate 4-Dimethylamino-4-phenylcyclohexanone (2.06 g, 9.5 mmoles) and 2-(benzofuran-3-yl)ethanethiol (1.70 g, crude product, according to NMR contains approx. 80% of the desired thiol) were initially introduced into abs. MC (25 ml) under argon. Methanesulfonic acid (680 µl, 10.45 mmoles) was then added. The mixture was stirred at room temperature for 4 days. For working up, water (15 ml) was added to the mixture. The aqueous phase was separated and extracted with MC (3×20 ml). The combined organic phases were washed with 2 M sulfuric acid and concentrated. The tacky, yellow residue was washed with diethyl ether (3×10 ml), and 2 M NaOH (20 ml) was then added. The resulting mixture was extracted with diethyl ether (3×15 ml). The ether phase was dried over sodium sulfate and concentrated. One of the two possible diastereoisomers of the target product was isolated from the resulting residue by column chromatography on silica gel with EA/ethanol in a volume ratio of 9:1 (112 mg of white solid, m.p. 160-165° C.). These 112 mg were dissolved in boiling ethanol (12 ml), an ethanolic solution (2 ml) of citric acid (62 mg, 0.324 mmole) was added and the mixture was stirred for 10 min. After cooling, the solvent was concentrated to approx. 5 ml and brought to approx. 5° C. The white precipitate which had precipitated out after approx. 6 hours was separated and dried. 112 mg of the citrate of 1,1-(3-dimethylamino-3-phenylpentamethylene)-3,4-dihydro-1H-9-oxa-2-thiafluorene were obtained (white solid, m.p. 207-209° C.).

Example 42

1,1-(3-Dimethylamino-3-phenylpentamethylene)-1,2,3,4-tetrahydrobenzo[4,5]furo[2,3-c]pyridine Citrate 2-(Benzofuran-3-yl)ethylamine (0.74 g, 4.6 mmoles) and 4-dimethylamino-4-phenylcyclohexanone (1.01 mg, 4.6 mmoles) were dissolved in methanol (35 ml) and the solution was stirred at room temperature for 24 hours. Thereafter, the mixture was evaporated to dryness. The residue was suspended in dry 1,2-dichloroethane (40 ml), and trifluoroacetic acid (4 ml) was added. The mixture was stirred at room temperature for 24 hours. For working up, the pH was adjusted to 11 with 5 M NaOH. After subsequent addition of EA (20 ml), a diastereoisomer of the target product precipitated out as a white precipitate. After 15 min, the precipitate was filtered out with suction and dried (867 mg, m.p. 193-196° C.). 400 mg of this were dissolved in hot ethanol (9 ml), and a similarly hot ethanolic solution of citric acid (212 mg, 1.1 mmol in 3 ml ethanol) was added. A white precipitate thereby precipitated out immediately. To bring the precipitation to completion, the mixture was left at approx. 5° C. for 4 hours. The resulting solid was filtered out with suction. The citrate of 1,1-(3-dimethylamino-3-phenylpentamethylene)-1,2,3,4-tetrahydrobenzo-[4,5]furo[2,3-c]pyridine was obtained in this way in a yield of 400 mg (white solid, m.p. 222-224° C.).

Example 43

6,6-(3-Dimethylamino-3-phenylpentamethylene)-1,2,3,4,-4-a,6,7,11c-octahydro-5-oxa-7-azabenzo[c]fluorene Citrate 4-Dimethylamino-4-phenylcyclohexanone (261 mg, 1.2 mmoles) and rac. 2-(1H-indol-3-yl)-cyclohexanol (260 mg, 1.2 mmoles) were initially introduced into abs. MC (20 ml) under argon. Trifluoromethanesulfonic acid trimethylsilyl ester (0.25 ml, 1.3 mmoles) was then added rapidly. The mixture was stirred at room temperature for 20 hours. For working up, 1 M NaOH (20 ml) was added to the reaction mixture, and the mixture was stirred for 30 min. The organic phase was separated, and the aqueous phase which remained was extracted with MC (3×30 ml). The combined organic phases were washed with water (2×30 ml), dried over sodium sulfate and concentrated to dryness. According to NMR, the solid formed from the residue after addition of methanol (approx. 25 ml) consisted of the two diastereoisomeric target products to be expected. To bring the precipitation to completion, the mixture was cooled to approx. 5° C. for 2 hours. The solid was then filtered out with suction and dried. The diastereoisomer mixture of the target product was obtained in this manner in a yield of 277 mg with a melting point of 150-170° C. 250 mg of this were dissolved in hot ethanol (200 ml), and a similarly hot solution of citric acid (192 mg, 1 mmole) in ethanol (20 ml) was added. No crystal formation was to be observed even after cooling the reaction mixture to approx. 5° C. The solution was therefore concentrated in vacuo to approx. 30 ml and left at approx. 5° C. for 3 days. 190 mg of the citrate of an approx. 60:40 mixture of the two diastereoisomeric 6,6-(3-dimethylamino-3-phenylpentamethylene)-1,2,3,4,4a,6,7,11c-octahydro-5-oxa-7-azabenzo[c]fluorenes were obtained (white solid, m.p. 184-192° C.).

Example 44

1,1-(3-Dimethylamino-3-phenylpentamethylene)-6-bromo-1,3,4,9-tetrahydropyrano[3,4-b]indole Hemicitrate 4-Dimethylamino-4-phenylcyclohexanone (326 mg, 1.5 mmoles) and 5-bromo-3-(2-trimethylsilanyloxy-ethyl)-1H-indole (468 mg, 1.5 mmoles) were initially introduced into MC (50 ml). Trifluoromethanesulfonic acid (0.145 ml, 1.51 mmoles) was then added rapidly. The mixture was stirred at room temperature for 15 hours. For working up, 2 M NaOH (10 ml) was added to the reaction mixture, and the mixture was stirred for 30 min. The organic phase was separated, and the aqueous phase was extracted with MC (3×30 ml). The combined organic phases were washed with water (2×30 ml) and dried over sodium sulfate. Methanol (30 ml) was added to the solid residue obtained after the solvent had been distilled off, and the mixture was heated, and stirred at room temperature for 15 hours. The solid suspended in methanol was filtered out with suction. One of the two possible diastereoisomers of the target product was obtained in this way in a yield of 583 mg (m.p. 271-281° C.). 550 mg of this were dissolved in hot ethanol (300 ml), and a similarly hot ethanolic citric acid solution (385 mg, 2 mmol in 20 ml) was added. A crystalline solid already precipitated out at the boiling point. To bring the crystallization to completion, the mixture was left at 5° C. for 12 hours. The solid formed was filtered off with suction. The hemicitrate of 1,1-(3-dimethylamino-3-phenylpentamethylene)-6-bromo-1,3,4,9-tetrahydropyrano[3,4-b]indole was obtained in this way in a yield of 510 mg (white solid, m.p. 262-267° C.).

Example 45

1,1-(3-Dimethylamino-3-phenylpentamethylene)-1,3,4,9-tetrahydropyrano[3,4-b]indol-6-ol Citrate 4-Dimethylamino-4-phenylcyclohexanone (490 mg, 2.26 mmoles) and 3-(2-hydroxyethyl)-1H-indol-5-ol (400 mg, 2.26 mmoles) were initially introduced into MC (150 ml). Trifluoromethanesulfonic acid trimethylsilyl ester (0.45 ml, 2.3 mmoles) was then added rapidly. The mixture was stirred at room temperature for 3 days. For working up, 1 M NaOH (30 ml) was added to the reaction mixture and the mixture was stirred for 30 min. The mixture was filtered, the organic phase was separated, and the aqueous phase which remained was extracted with MC (3×60 ml). The combined organic phases were washed with water (2×30 ml) and dried over sodium sulfate. Methanol (50 ml) was added to the solid residue obtained after the solvent had been distilled off. The clear solution formed was concentrated to approx. 10 ml and left to stand at 5° C. for 2 hours. The solid which had precipitated from methanol was filtered out with suction. One of the two diastereoisomeric target products was obtained (180 mg, m.p. 252-257° C.). 160 mg of this were dissolved in hot ethanol (20 ml), and a similarly hot ethanolic citric acid solution (150 mg, 0.78 mmol in 10 ml) was added. A crystalline solid already precipitated out at the boiling point. To bring the crystallization to completion, the mixture was left at 5° C. for 20 hours. The resulting solid was filtered out with suction. The citrate of 1,1-(3-dimethylamino-3-phenylpentamethylene)-1,3,4,9-tetrahydropyrano-[3,4-b]indol-6-ol was obtained in this way in a yield of 125 mg (white solid, m.p. 248-254° C.).

Example 46

(3S)-1,1-(3-Dimethylamino-3-phenylpentamethylene)-3,4-dihydro-3-methoxycarbonyl-1H-2,9-diazafluorene citrate 4-Dimethylamino-4-phenylcyclohexanone (434.8 mg, 2 mmoles) and L-tryptophan methyl ester ((2S)-2-amino-3-(1H-indol-3-yl)propionic acid methyl ester, 436.5 mg, 2 mmoles) were dissolved in dry methanol (20 ml). After a reaction time of 24 hours, the methanol was distilled off and the yellow, oily residue was suspended in 1,2-dichloroethane (20 ml). Trifluoroacetic acid (2 ml) was added to the reaction mixture and the mixture was stirred at room temperature for 18 hours. For working up, the mixture was diluted with water (20 ml) and adjusted to pH 11 with NaOH (5 mole/l). After addition of EA (20 ml), a white solid precipitated out, and was filtered out with suction. The solid was washed with water (3×5 ml) and dried. It was a mixture of the diastereoisomers of the target product (70% non-polar:30% polar) which it was possible to obtain as a white solid in a yield of 600 mg. These 600 mg were dissolved in hot ethanol (30 ml), and a similarly hot solution of citric acid (276 mg, 1.44 mmoles) in ethanol (5 ml) was added. After cooling to approx. 5° C., the mixture was left to stand for 4 hours. The resulting solid was filtered out with suction. It was possible to obtain the citrate of (3S)-1,1-(3-dimethylamino-3-phenylpenta-methylene)-3,4-dihydro-3-methoxycarbonyl-1H-2,9-diazafluorene in this way as an approx. 70:30 mixture of the more non-polar and more polar diastereoisomer in a yield of 875 mg (white solid, m.p. 193-196° C.).

Example 47

(3S)-1,1-(3-Dimethylamino-3-phenylpentamethylene)-3,4-dihydro-1H-2,9-diazafluorene-3-methanol Citrate 4-Dimethylamino-4-phenylcyclohexanone (434.8 mg, 2 mmoles) and L-tryptophanol ((2S)-2-amino-3-(1H-indol-3-yl)-propan-1-ol, 380.5 mg, 2 mmoles) were dissolved in dry methanol (20 ml). After a reaction time of 24 hours, methanol was distilled off and the yellow, oily residue was suspended in 1,2-dichloroethane (20 ml). Trifluoroacetic acid (2 ml) was added to the reaction mixture and the mixture was stirred at room temperature for 18 hours. For working up, the mixture was diluted with water (20 ml) and adjusted to pH 11 with NaOH (5 mole/l). After addition of EA (20 ml), a white solid precipitated out, and was filtered out with suction. The solid was washed with water (3×5 ml) and dried. It was a mixture of the diastereoisomers of the target product (30% non-polar: 70% polar), which it was possible to obtain as a white solid with a yield of 700 mg. These 700 mg were dissolved in hot ethanol (40 ml), and a similarly hot solution of citric acid (346 mg, 1.8 mmoles) in ethanol (5 ml) was added. After cooling to approx. 5° C., the mixture was left to stand for 4 hours. The resulting solid was filtered out with suction. It was possible to obtain the citrate of (3S)-1,1-(3-dimethylamino-3-phenylpentamethylene)-3,4-dihydro-1H-2,9-diazafluorene-3-methanol in this way in a yield of 1.0 g as an approx. 30:70 mixture of the more non-polar and more polar diastereoisomer (white solid, m.p. 265-270° C.).

Example 48

1,1-(3-Dimethylamino-3-phenylethyl-pentamethylene)-3,4-dihydro-1H-2,9-diazafluorene 4-Dimethylamino-4-phenethyl-cyclohexanone (5 g, 20 mmoles) and tryptamine (3.2 g, 20 mmoles) were dissolved in dry methanol (200 ml). After a reaction time of 24 hours, methanol was distilled off and the yellow, oily residue was suspended in 1,2-dichloroethane (200 ml). Trifluoroacetic acid (20 ml) was added to the reaction mixture and the mixture was stirred at room temperature for 2 hours. For working up, the mixture was diluted with water (100 ml) and adjusted to pH 11 with NaOH (5 mole/l). After addition of EA (50 ml), a white solid precipitated and was filtered out with suction. The solid was washed with water (3×25 ml) and dried over sodium sulfate. It was a mixture of the diastereoisomers of the target product (10% non-polar:90% polar), which was obtained as a white solid (m.p. 225-230° C.) in a yield of 4.42 g.

Example 49

1,1-(3-Methylamino-3-phenylpentamethylene)-6-fluoro-1,3,4,9-tetrahydropyrano[3,4-b]indole Hemicitrate 4-Methylamino-4-phenyl-cyclohexanone (406 mg, 2 mmoles) and 5-fluoro-3-(2-trimethylsilanyloxyethyl)-1H-indole (503 mg, 2 mmoles) were initially introduced into MC (50 ml). Trifluoromethanesulfonic acid (0.18 ml, 2.03 mmoles) was then added rapidly. The mixture was stirred at room temperature for 20 hours. For working up, 2 M NaOH (20 ml) was added to the reaction mixture, and the mixture was stirred for 20 min. The organic phase was separated, and the aqueous phase which remained was extracted with MC (3×30 ml). The combined organic phases were washed with water (2×30 ml) and dried over sodium sulfate. Methanol (25 ml) was added to the solid residue obtained after the solvent had been distilled off, and the mixture was heated, and then stirred at room temperature for 4 hours. The solid suspended in methanol was filtered out with suction. One of the two possible diastereoisomers of the target product was obtained in this manner in a yield of 490 mg (m.p. 248-252° C.). 450 mg of this were dissolved in hot ethanol (50 ml), and a similarly hot ethanolic citric acid solution (384 mg, 2 mmol in 10 ml) was added. A crystalline solid already precipitated out at the boiling point. To bring the crystallization to completion, the mixture was left at approx. 5° C. for 15 hours. The resulting solid was filtered out with suction. The hemicitrate of 1,1-(3-methylamino-3-phenylpenta-methylene)-6-fluoro-1,3,4,9-tetrahydropyrano[3,4-b]indole was obtained in this way in a yield of 550 mg (white solid, m.p. 226-228° C.).

Example 50

1,1-(3-Dimethylamino-3-(4-fluorophenyl)pentamethylene)-3,4-dihydro-1H-2,9-dithiafluorene Methanesulfonate 4-Dimethylamino-4-(4-fluorophenyl)cyclohexanone (353 mg, 1.5 mmoles) and 2-(benzo[b]thiophen-3-yl)ethanethiol (297 mg in 11.5 ml of solution, 1.5 mmoles) were initially introduced into absolute MC (20 ml) under argon. Methanesulfonic acid (194.5 µl, 3.0 mmoles) was then added. The mixture was stirred at room temperature for 24 hours. A further 100 µl methanesulfonic acid were added to the reaction mixture and the mixture was stirred again at room temperature for 20 hours. For working up, water (4 ml) was added to the clear reaction mixture, and the mixture was stirred for 1 hour. A precipitate thereby precipitated out. The precipitate was filtered out with suction, washed with water (2×1 ml) and diethyl ether (2×2 ml) and dried. The white solid was the methanesulfonate of 1,1-(3-dimethylamino-3-(4-fluorophenyl)penta-methylene)-3,4-dihydro-1H-2,9-dithiafluorene (262 mg, m.p. 256-258° C.).

Example 51

1,1-(3-Dimethylamino-3-phenylpentamethylene)-3,4-dihydro-1H-2,9-dithiafluorene Citrate 4-Dimethylamino-4-phenethyl-cyclohexanone (326 mg, 1.5 mmoles) together with 2-(benzo[b]thiophen-3-yl)ethanethiol (297 mg, 1.5 mmoles) were initially introduced into absolute methylene chloride (20 ml) under argon, and methanesulfonic acid (195 µl, 3.0 mmoles) was added. The mixture was stirred at room temperature for 24 hours. A further 100 μl methanesulfonic acid were added to the reaction mixture, and the mixture was stirred again at room temperature for 20 hours. For working up, water (5 ml) was added to the clear reaction mixture and the mixture was stirred for 1 hour. It was then adjusted to pH 11 with 1 M NaOH and diluted with MC (5 ml). The phases were separated. The aqueous phase was extracted with MC (3×10 ml). The extracts were combined, washed once with saturated NaCl solution and dried over sodium sulfate. After the MC had been distilled off, the residue was a yellow solid. For purification, ethanol (5 ml) was added to this and the mixture was boiled under reflux for 10 min. After cooling to room temperature, the mixture was stirred for 24 hours. The precipitate present was filtered out with suction, washed with cold ethanol (3×2 ml) and dried. One of the two possible free bases of the target product (335 mg, beige, 57%) was obtained in this way with a melting point of 210-214° C. 120 mg of this were dissolved in hot ethanol (40 ml), citric acid (59.2 mg, 0.308 mmol, dissolved in 1 ml ethanol) was added, and the mixture was stirred at 65° C. for 10 min. After cooling to room temperature, the mixture was stirred for 20 hrs. Since no precipitate had precipitated out, the ethanol was concentrated down to 2 ml and diethyl ether (30 ml) was slowly added. The resulting solid was filtered out with suction, washed with diethyl ether (3×2 ml) and then dried. 152 mg of the citrate of 1,1-(3-dimethylamino-3-phenylpentamethylene)-3,4-dihydro-1H-2,9-dithiafluorene were obtained as a white solid (m.p. 125-128° C.).

Example 52

1,1-(3-Dimethylamino-3-phenylpentamethylene)-2-oxo-1,3,4,9-tetrahydro-2-thia-9-azafluorene Citrate 1,1-(3-Dimethylamino-3-phenylpentamethylene)-3,4-dihydro-1H-2,9-dithiafluorene (200 mg, 0.53 mmole) was suspended in glacial acetic acid (3 ml), 30 percent strength hydrogen peroxide (200 μl) were added dropwise, while stirring, and the mixture was stirred at room temperature for 2 hours. For working up, 5 ml water were added to the reaction mixture and the mixture was rendered alkaline with 5 M NaOH. A suspension thereby formed, which did not dissolve completely even after the addition of EA (50 ml). The precipitate was filtered out with suction, washed with water (2×1 ml) and discarded. The aqueous mother liquor was brought to pH 11 with 5 M NaOH. A white precipitate thereby precipitated out. The solid was filtered out with suction, washed with water (1×2 ml) and ether (3×1 ml) and dried. 76 mg 1,1-(3-dimethylamino-3-phenylpentamethylene)-2-oxo-1,3,4,9-tetrahydro-2-thia-9-azafluorene were obtained (m.p. 188-192° C.). 61 mg of this were dissolved in hot ethanol (8 ml), citric acid (32.8 mg, 0.17 mmole) was added and the mixture was stirred at 65° C. for 10 min. After cooling to room temperature the mixture was stirred for 20 hours. Because only little white precipitate had precipitated out, the ethanol was concentrated down to 2 ml and ether (30 ml) was slowly added. The resulting solid was filtered out with suction, washed with ether (3×2 ml) and then dried. 74 mg of the citrate of 1,1-(3-dimethylamino-3-phenylpentamethylene)-2-oxo-1,3,4,9-tetrahydro-2-thia-9-azafluorene were obtained (white solid, m.p. 162-167° C.).

Example 53

1,1-(3-Dimethylamino-3-benzylpentamethylene)-3,4-dihydro-1H-2,9-diazafluorene

4-Benzyl-4-dimethylaminocyclohexanone (3.47 g, 15 mmole) and tryptamine (2.40 g, 15 mmoles) were dissolved in dry methanol (150 ml) under argon. After a reaction time of 24 hours, methanol was distilled off, and the residue was suspended in 1,2-dichloroethane (150 ml). Trifluoroacetic acid (15 ml) was added to the reaction mixture, and the mixture was stirred at room temperature for 2 hours. For working up, water (100 ml) was added to the mixture and the mixture was adjusted to pH 11 with NaOH (5 mole/l). After addition of EA (70 ml), a white solid precipitated out on stirring, and was filtered out with suction over a frit. The solid was washed with water (5×20 ml) and dried. A diastereoisomer mixture of 1,1-(3-dimethylamino-3-benzylpentamethylene)-3,4-dihydro-1H-2,9-diazafluorene (15% non-polar: 85% polar) was obtained as a white solid with a melting point of 195-200° C. and a yield of 3.0 g.

Preparation of the Structural Units Used:

Trimethylsilyl ether—General instructions based on the example of 3-(2-trimethylsilanyloxyethyl)-1H-indole Tryptophol (4.83 g, 30 mmoles) was initially introduced into dry THF (80 ml), and first hexamethyldisilazane (30 ml, 141 mmoles) and then chlorotrimethylsilane (8 ml, 62.6 mmoles) were added at room temperature. The mixture was stirred at room temperature for 20 hours. The THF was distilled off, and saturated sodium bicarbonate solution was added to the residue until a basic reaction was obtained. The aqueous solution was extracted with ether. The organic phase was washed with water and dried over sodium sulfate. After removal of the solvent, the trimethylsilyl ether was obtained in a yield of 6.99 g as a crystalline solid (m.p. 47-48° C.).

2-(Benzofuran-3-yl)ethanethiol

Triphenylphosphane dibromide (5.52 g, 14.4 mmoles) was suspended in abs. acetonitrile (15 ml) under argon, the suspension was brought to 19° C. in a water-bath and 2-(benzofuran-3-yl)ethanol (2.11 g, 13.1 mmoles) in abs. acetonitrile (7 ml) was added in the course of 15 min. During the addition the temperature of the reaction mixture was kept between 19 and 21° C. The mixture was then left to stand for 12 hours without further cooling. The reaction mixture was filtered and the filtrate obtained was concentrated. The residue obtained was taken up in cyclohexane (20 ml), and the mixture was filtered over a silica gel layer (15 g) about 3 cm thick. The silica gel was washed with cyclohexane (5×20 ml) and the filtrate obtained was concentrated. 2.47 g 3-(2-bromoethyl)benzofuran were obtained as a yellowish oil.

Sodium thiosulfate pentahydrate (5.44 g, 21.9 mmoles) was dissolved in water (22 ml), and the 3-(2-bromoethyl)benzofuran (2.90 g, 12.9 mmoles), dissolved in ethanol (40 ml), was added in the course of 10 min, while stirring. The reaction mixture was then boiled under reflux for 4 hours. For working up, the ethanol contained in the solvent mixture was distilled off in vacuo. The aqueous residue was extracted with diethyl ether (3×20 ml) and the organic phase was washed with water (2×20 ml). The combined aqueous phases were evaporated on a rotary evaporator. The white-yellowish residue (3.63 g) obtained in this way consists of the sodium salt of thiosulfuric acid S-[2-benzofuran-3-yl)-ethyl]ester ("Bunte salt") contains an undefined residual amount of water. The subsequent conversion to the thiol was carried out without further purification. The resulting 3.63 g of the sodium salt of thiosulfuric acid S-[2-benzofuran-3-yl)ethyl]ester were suspended in 50 wt. % strength phosphoric acid (60 ml) under argon. The reaction mixture obtained was then covered with a layer of diethyl ether (75 ml) and the mixture was heated under reflux (7 hours), with vigorous stirring, until solid was no longer to be observed in the aqueous phase. After cooling, the two phases were separated and the aqueous phase was extracted with diethyl ether (4×15 ml). The combined ethereal phases were washed with water (2×10 ml) and dried over sodium sulfate. According to NMR, the residue (yellowish oil, 1.71 g) obtained after removal of the diethyl ether contained approx. 80% of the desired 2-(benzo-furan-3-yl) ethanethiol, which was employed without further purification.

3-(2-Hydroxy-ethyl)-1H-indol-5-ol (5-hydroxy-tryptophol)

5-Hydroxyindol-3-acetic acid (1.91 g, 10 mmoles) was initially introduced into MC (40 ml) under argon, the mixture was cooled to −78° C. and diisopropylaluminium hydride (0.2 M in toluene, 40 ml, 48 mmoles) was added in the course of 20 min, while stirring. When the addition of the reducing agent had ended, the mixture was allowed to come to RT in the course of 5 hours and was then left at RT for a further hour. For working up, methanol (2 ml) was cautiously added to the reaction mixture. The previously continuously solid mass became liquid again during the addition. Saturated NaCl solution (10 ml) was now added in portions to the mixture. The resulting mixture was left to stand overnight and then filtered off with suction over kieselguhr. The filter cake was washed with a total of 400 ml MC. The filtrate was dried over sodium sulfate and concentrated. 730 mg 3-(2-hydroxy-ethyl)-1H-indol-5-ol were obtained (m.p. 98-102° C.).

Overview of the Examples:

| Example No. | Structure | Salt form | Comments |
|---|---|---|---|
| 1 | 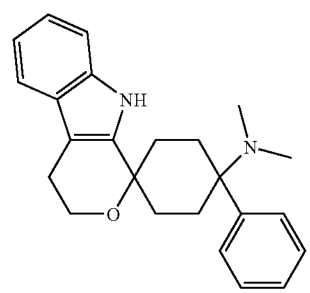 | hydrochloride | more non-polar diastereomer |
| 2 | 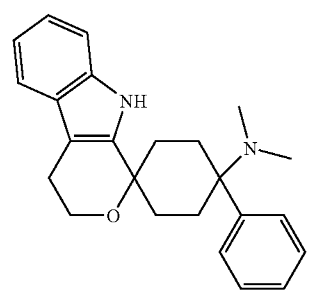 | hydrochloride | more polar diastereomer |
| 3 | 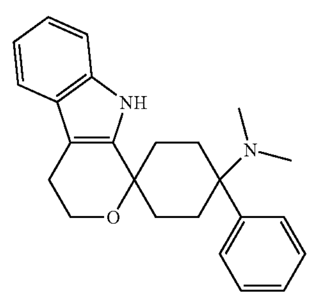 | hemicitrate | more non-polar diastereomer |
| 4 | 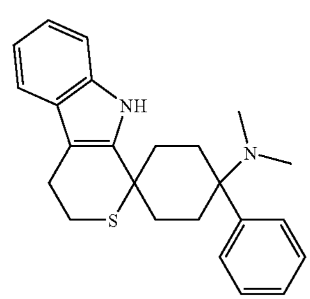 | hemicitrate | more non-polar diastereomer |

| Example No. | Structure | Salt form | Comments |
| --- | --- | --- | --- |
| 5 | 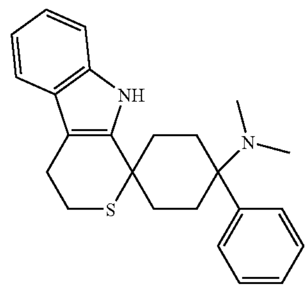 | citrate | more polar diastereomer |
| 6 | 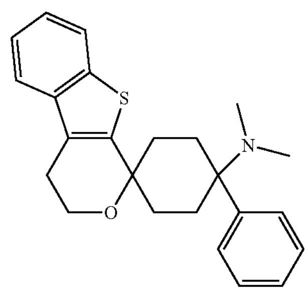 | tartrate | one of 2 diastereomers |
| 7 | 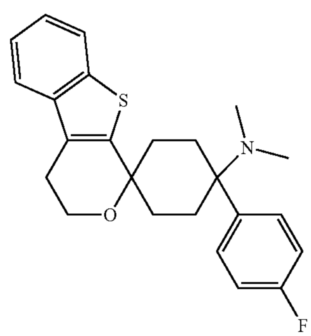 | triflate | one of 2 diastereomers |
| 8 | 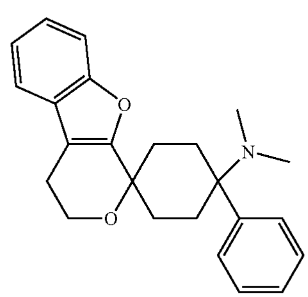 | hemicitrate | one of 2 diastereomers |
| 9 | 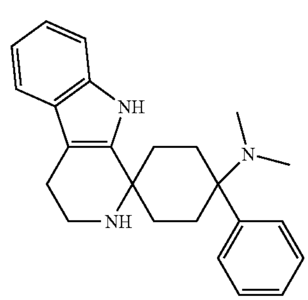 | dihydrochloride | 70:30 more non-polar:more polar d. |

-continued

| Example No. | Structure | Salt form | Comments |
|---|---|---|---|
| 10 | 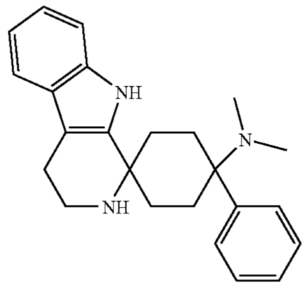 | dihydrochloride | more polar diastereomer |
| 11 | 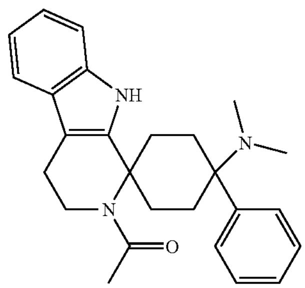 | hydrochloride | more non-polar diastereomer |
| 12 | 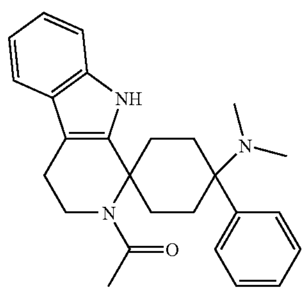 | hydrochloride | more polar diastereomer |
| 13 | 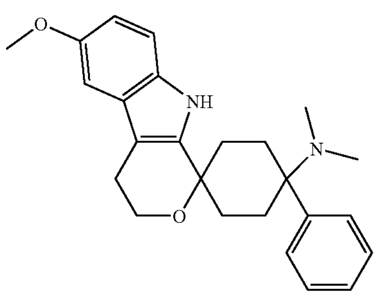 | hydrochloride | more non-polar diastereomer |
| 14 | 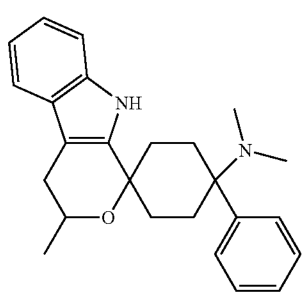 | hemicitrate | more non-polar diastereomer |

-continued

| Example No. | Structure | Salt form | Comments |
|---|---|---|---|
| 15 | 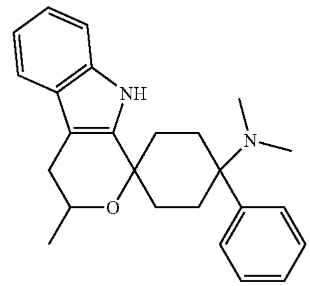 | citrate | more polar diastereomer |
| 16 | 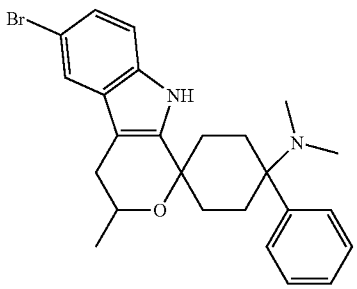 | hemicitrate | one of 2 diastereomers |
| 17 | 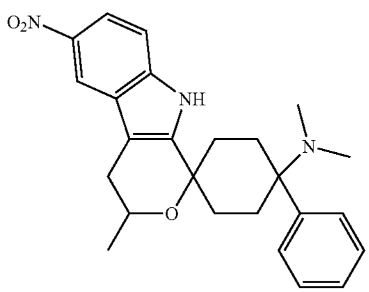 | citrate | more non-polar diastereomer |
| 18 | 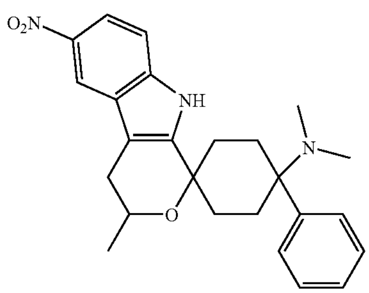 | citrate | more polar diastereomer |
| 19 | 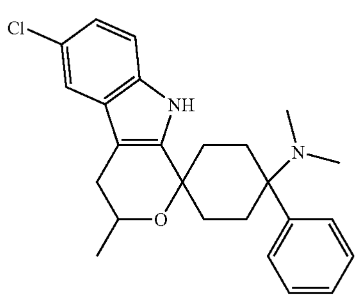 | citrate | more non-polar diastereomer |

-continued
| Example No. | Structure | Salt form | Comments |
|---|---|---|---|
| 20 | 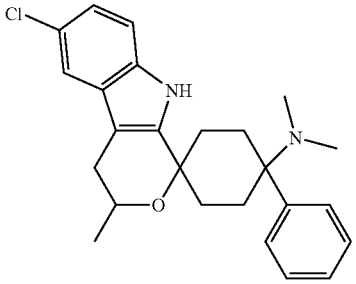 | citrate | more polar diastereomer |
| 21 | 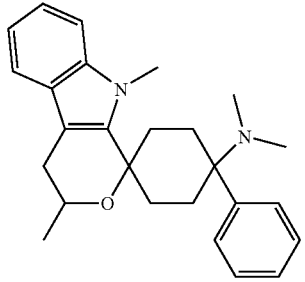 | citrate | one of 2 diastereomers |
| 22 | 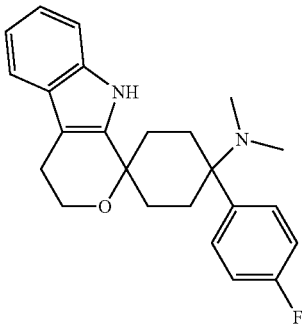 | hemicitrate | one of 2 diastereomers |
| 23 | 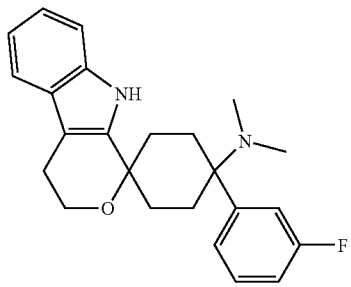 | hemicitrate | one of 2 diastereomers |
| 24 | 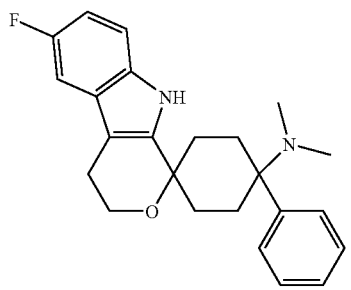 | hemicitrate | more non-polar diastereomer |

-continued

| Example No. | Structure | Salt form | Comments |
|---|---|---|---|
| 25 | 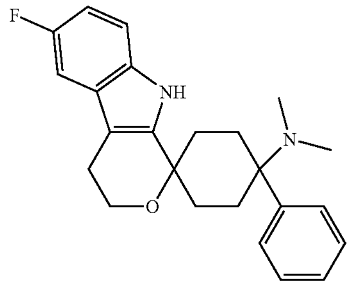 | hemicitrate | more polar diastereomer |
| 26 | 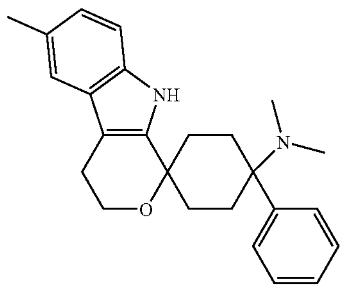 | hemicitrate | one of 2 diastereomers |
| 27 | 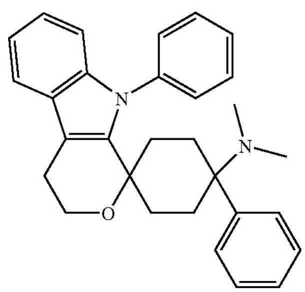 | citrate | one of 2 diastereomers |
| 28 | 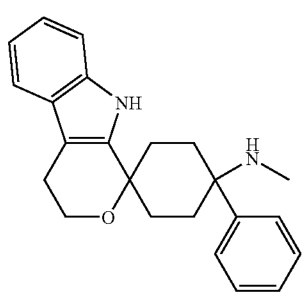 | hemicitrate | one of 2 diastereomers |
| 29 | 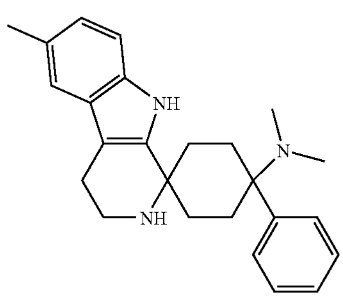 | citrate | more polar diastereomer |

-continued

| Example No. | Structure | Salt form | Comments |
| --- | --- | --- | --- |
| 30 | 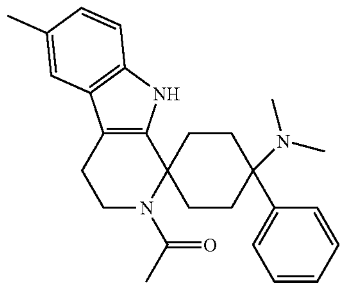 | citrate | more polar diastereomer |
| 31 | 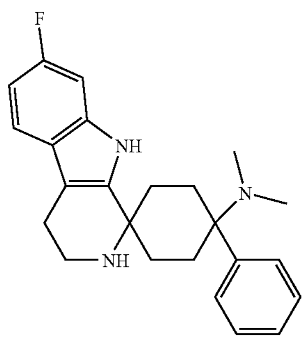 | citrate | more polar diastereomer |
| 32 | 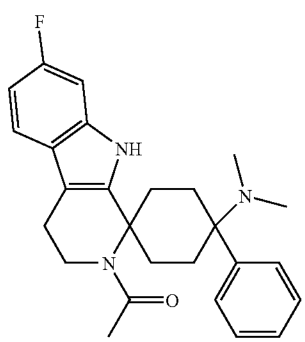 | citrate | more non-polar diastereomer rotamers |
| 33 | 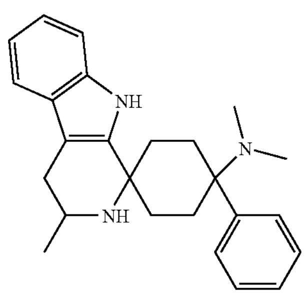 | citrate | one of 2 diastereomers |
| 34 | 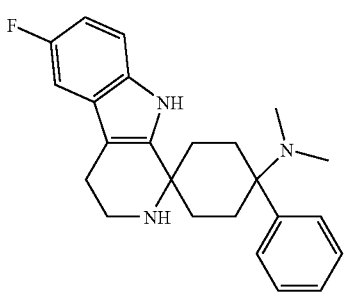 | dihydrochloride | mixture of the diastereomers |

-continued

| Example No. | Structure | Salt form | Comments |
| --- | --- | --- | --- |
| 35 | 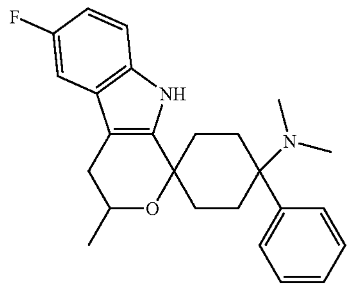 | hemicitrate | one of 2 diastereomers |
| 36 | 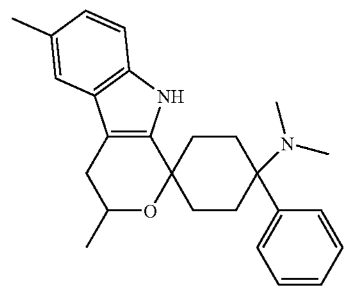 | hemicitrate | more non-polar diastereomer |
| 37 | 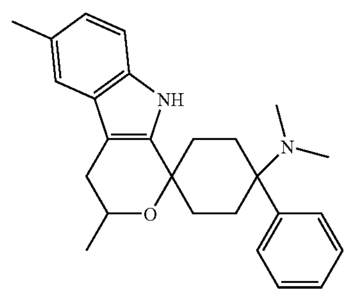 | citrate | more polar diastereomer |
| 38 | 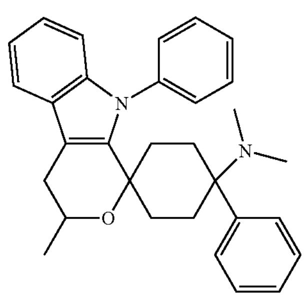 | citrate | one of 2 diastereomers |
| 39 | 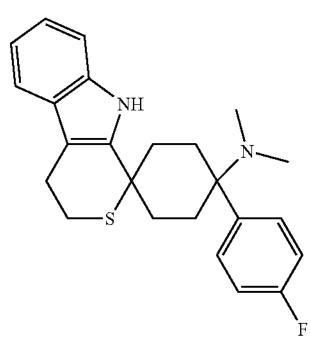 | methanesulfonate | one of 2 diastereomers |

-continued

| Example No. | Structure | Salt form | Comments |
|---|---|---|---|
| 40 | 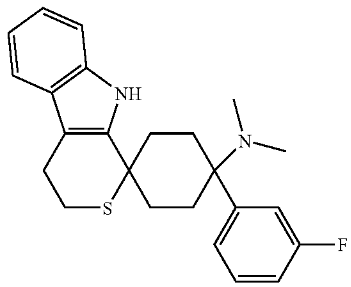 | methanesulfonate | one of 2 diastereomers |
| 41 | 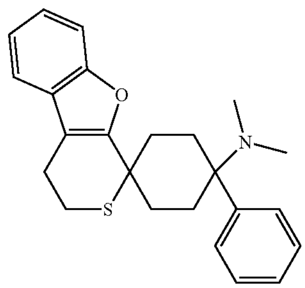 | citrate | |
| 42 | 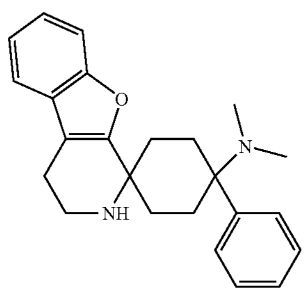 | citrate | one of 2 diastereomers |
| 43 | 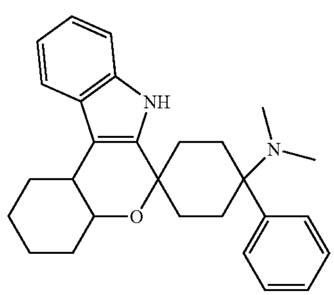 | citrate | mixture of the diastereomers |
| 44 | 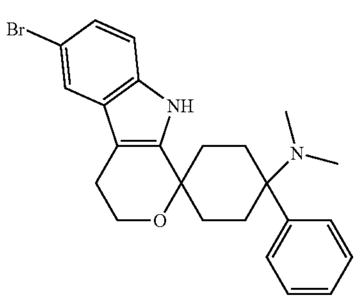 | hemicitrate | one of 2 diastereomers |

-continued

| Example No. | Structure | Salt form | Comments |
|---|---|---|---|
| 45 | 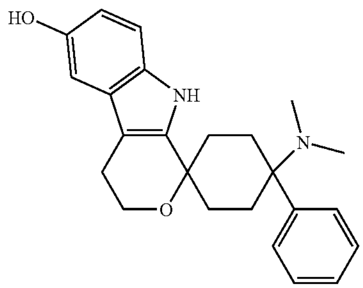 | citrate | one of 2 diastereomers |
| 46 | 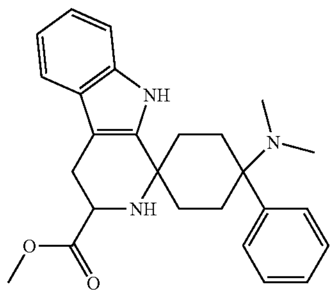 | citrate | 70:30 more non-polar:more polar diastereomer |
| 47 | 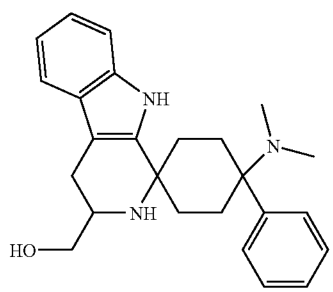 | citrate | 30:70 more non-polar:more polar diastereomer |
| 48 | 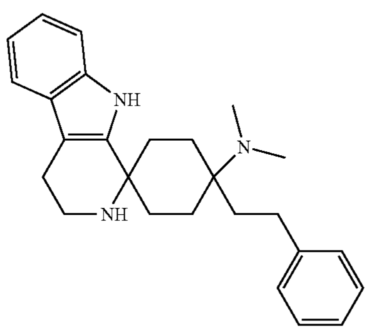 | base | |
| 49 | 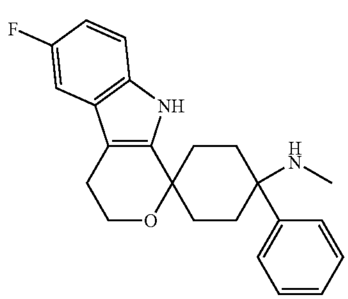 | hemicitrate | one of 2 diastereomers |

-continued

| Example No. | Structure | Salt form | Comments |
|---|---|---|---|
| 50 | 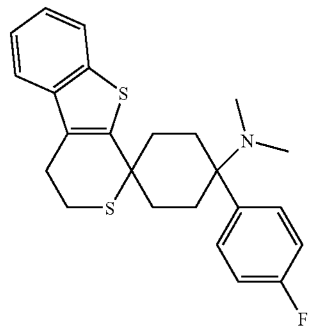 | methanesulfonate | one of 2 diastereomers |
| 51 | 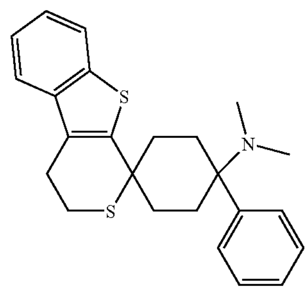 | citrate | one of 2 diastereomers |
| 52 | 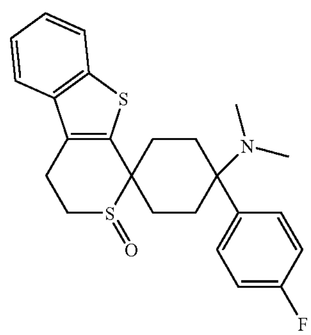 | citrate | one of 2 diastereomers |
| 53 | 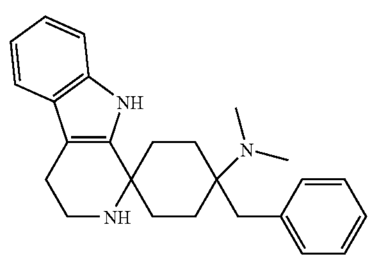 | base | 15:85 more non-polar:more polar diastereomer |

Investigations of the Activity of the Compounds According to the Invention:

The data recorded in the following assays and models are summarized in Table 1.

Measurement of the ORL1 Binding

The cyclohexane derivatives of the general formula I were investigated in a receptor binding assay with $^3$H-nociceptin/orphanin FQ with membranes from recombinant CHO-ORL1 cells. This test system was conducted in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with in each case 20 μg of membrane protein per 200 μl batch in 50 mM hepes, pH 7.4, 10 mM MgCl$_2$ and 1 mM EDTA. The binding to the ORL1 receptor was determined using in each case 1 mg WGA-SPA beads (Amersham-Pharmacia, Freiburg) by incubation of the batch for one hour at room temperature and subsequent measurement in a Trilux scintillation counter (Wallac, Finland). The affinity is stated in Table 1 as the nanomolar $K_i$ value in or % inhibition at c=1 μM.

Measurement of the μ Binding

The receptor affinity for the human μ-opiate receptor was determined in a homogeneous batch in microtitre plates. For this, dilution series of the particular spirocyclic cyclohexane derivative to be tested were incubated in a total volume of 250 μl for 90 minutes at room temperature with a receptor membrane preparation (15-40 μg protein per 250 μl incubation batch) of CHO-K1 cells, which express the human β-opiate receptor (RB-HOM receptor membrane preparation of NEN, Zaventem, Belgium), in the presence of 1 nmol/l of the radioactive ligand [$^3$H]-naloxone (NET719, NEN, Zaventem, Belgium) and of 1 mg WGA-SPA beads (wheat germ agglutinin SPA beads from Amersham/Pharmacia, Freiburg, Germany). 50 mmoles/l Tris-HCl supplemented with 0.05 wt. % sodium azide and with 0.06 wt. % bovine serum albumin was used as the incubation buffer. 25 µmoles/l naloxone was additionally added for determination of the non-specific binding. When the ninety minutes of incubation time had ended, the microtitre plates were centrifuged off at 1,000 g for 20 minutes and the radioactivity was measured in a β-counter (Microbeta-Trilux, PerkinElmer Wallac, Freiburg, Germany). The percentage displacement of the radioactive ligand from its binding to the human µ-opiate receptor at a concentration of the test substances of 1 µmole/l was determined and was stated as the percentage inhibition (% inhibition) of the specific binding. In some cases, on the basis of the percentage displacement by different concentrations of the compounds of the general formula I to be tested, $IC_{50}$ inhibitory concentrations which cause 50 percent displacement of the radioactive ligand were calculated. By conversion by means of the Cheng-Prusoff relationship, Ki values were obtained for the test substances.

Testing for Analgesia in the Writing Test in Mice

The analgesic activity was investigated using the phenylquinone-induced writhing test in mice (modified in accordance with I. C. Hendershot and J. Forsaith (1959) J. Pharmacol. Exp. Ther. 125, 237-240). Male NMRI mice weighing 25 to 30 g were used for this. Groups of 10 animals per substance dose received 0.3 ml/mouse of a 0.02% strength aqueous solution of phenylquinone (phenylbenzoquinone, Sigma, Deisenhofen; preparation of the solution with the addition of 5% ethanol and storage in a water-bath at 45° C.) administered intraperitoneally 10 minutes after intravenous administration of the test substances. The animals were placed individually in observation cages. The number of pain-induced stretching movements (so-called writhing reactions, i.e. straightening of the body with stretching of the rear extremities) was counted by means of a push-button counter 5 to 20 minutes after the administration of phenylquinone. Animals which receive only physiological saline solution were also run as a control. All the substances were tested in the standard dosage of 10 mg/kg. The percentage inhibition (% inhibition) of the writhing reaction by a substance was calculated according to the following formula:

$$\% \text{ inhibition} = 100 - \frac{\text{writhing reactions of the treated animals}}{\text{writhing reactions of the control animals}} * 100$$

For some substances, the $ED_{50}$ values with the 95% confidence range of the writhing reaction was calculated by means of regression analysis (evaluation program Martens EDV Service, Eckental) from the dose-dependent decrease in the writhing reactions compared with phenylquinone control groups investigated in parallel.

Testing for Analgesia in the Tail Flick Test in Mice

The mice were each placed individually in a test cage and the base of the tail was exposed to the focused heat ray of an electric lamp (tail flick model 50/08/1.bc, Labtec, Dr. Hess). The lamp intensity was adjusted such that the time from switching on of the lamp to sudden pulling away of the tail (pain latency) in untreated mice was 3 to 5 sec. Before administration of the solutions containing the compound according to the invention or the particular comparison solutions, the mice were pretested twice within five minutes and the mean of these measurements was calculated as the pretest mean.

The solutions of the compound of the general formula I according to the invention and the comparison solutions were then administrated intravenously. The pain measurement was performed in each case 10, 20, 40 and 60 minutes after the intravenous administration. The analgesic action was determined as the increase in the pain latency (% of the maximum possible antinociceptive effect) according to the following equation:

$$[(T_1-T_0)/(T_2-T_0)] \times 100$$

In this equation, the time $T_0$ is the latency time before the administration, the time $T_1$ is the latency time after the administration of the active compound combination and the time $T_2$ is the maximum duration of exposure (12 seconds).

TABLE 1

| Example No. | ORL1 Ki[nM] or % inhibition [1 µM] | µ Ki[nM] or % inhibition [1 µM] | Writhing (mouse, i.v.) $ED_{50}$ [mg/kg] or % inhibition (dose [mg/kg]) | Tail flick (mouse, i.v.) $ED_{50}$ [mg/kg] or % inhibition (dose [mg/kg]) |
|---|---|---|---|---|
| 1 | 0.3 | 0.6 | | 0.0035 |
| 2 | | 310 | | |
| 3 | 0.6 | 1.3 | | 0.0182 (i.p.) |
| 4 | 3.7 | 3.1 | | |
| 6 | | 53% | | |
| 7 | | 76% | | |
| 8 | | 80% | 89% (10) | |
| 9 | 0.26 | 0.36 | | 94% (1) |
| 10 | 3.4 | 4.5 | | |
| 11 | 2.9 | 4.4 | | |
| 12 | 2.4 | 2.2 | | 67% (0.1) |
| 13 | 5.8 | 2.0 | 0.0033 | 0.02 |
| 14 | 1.2 | 12.0 | | 0.029 |
| 15 | 42.0 | 58.0 | | |
| 16 | 23.0 | 14.0 | | |
| 17 | 70.0 | 6.6 | | |
| 18 | 29.0 | 25.0 | | |
| 19 | 91% | 95% | | |
| 20 | 56% | 75% | | |
| 21 | | 75% | | |
| 22 | 3.2 | 7.2 | | 100% (0.1) |
| 23 | 1.2 | 2.1 | | 0.018 |
| 24 | 2.9 | 1.5 | | 0.019 |
| 25 | 22.0 | 12.0 | | 100% (1) |
| 26 | 4.5 | 2.7 | | 0.039 |
| 28 | 1.4 | 1.2 | | 0.042 |
| 29 | 32.0 | 15.0 | | |
| 30 | 58% | 99% | | |
| 31 | 6.9 | 17.0 | | |
| 32 | 1.1 | 1.7 | | 100% (0.1) |
| 33 | 0.5 | 0.5 | | 100% (1) |
| 34 | 1.4 | 0.7 | | 89% (1) |
| 35 | 83.0 | 61.0 | | |
| 36 | 4.4 | 14.0 | | 100% (1) |
| 37 | 56% | 90% | | |
| 38 | | 43% | | |
| 39 | | 90% | | |
| 40 | 55% | 100% | | |
| 42 | 75% | 86% | | |
| 43 | 91% | 96% | | |
| 44 | 52.0 | 19.0 | | |
| 45 | 1.6 | 1.1 | | 0.013 |
| 46 | 0.9 | 2.3 | | |
| 47 | 99% | 2.7 | | |
| 49 | 10.0 | 6.8 | | 0.22 |
| 52 | 62.0 | 58.0 | | |
| 53 | 1.1 | 0.6 | | |

Example 54

Parenteral Solution of a Spirocyclic Cyclohexane Derivative According to the Invention 38 g of one of the spirocyclic cyclohexane derivatives according to the invention, here Example 3, are dissolved in 1 l of water for injection purposes at room temperature and the solution is then adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A pharmaceutical composition comprising at least one spirocyclic cyclohexane compound corresponding to formula I

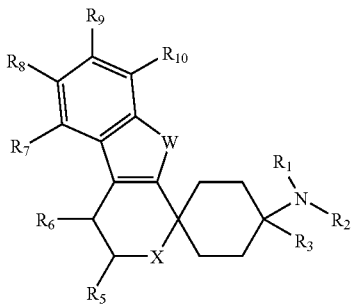

wherein
  $R^1$ and $R^2$ independently of one another represent H, $C_{1-5}$-alkyl, branched or unbranched, saturated or unsaturated, unsubstituted or mono- or polysubstituted, or CHO; or
  $R^1$ and $R^2$ together represent $CH_2CH_2OCH_2CH_2$, $CH_2CH_2NR^{11}CH_2CH_2$ or $(CH_2)_{3-6}$,
  wherein
    $R^{11}$ denotes H; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl-, or heteroaryl, in each case mono- or polysubstituted or unsubstituted; or aryl, $C_{3-8}$-cycloalkyl or heteroaryl which are bonded via $C_{1-3}$-alkyl and are in each case mono- or polysubstituted or unsubstituted;
  $R^3$ represents $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl, in each case unsubstituted or mono- or polysubstituted; aryl or $C_{3-8}$-cycloalkyl which are bonded via a $C_{1-3}$-alkylene group and are in each case unsubstituted or mono- or polysubstituted;
  W represents $NR^4$, O or S;
    wherein
      $R^4$ denotes H; $C_{1-5}$-alkyl, saturated or unsaturated, branched or unbranched, unsubstituted or mono- or polysubstituted; aryl, or heteroaryl, in each case substituted or unsubstituted; aryl, heteroaryl or cycloalkyl which are bonded via a $C_{1-3}$-alkyl group and are in each case mono- or polysubstituted or unsubstituted; $COR^{12}$; $SO_2R^{12}$,
      wherein
        $R^{12}$ denotes H; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl-, or heteroaryl, in each case mono- or polysubstituted or unsubstituted; or aryl, $C_{3-8}$-cycloalkyl or heteroaryl which are bonded via $C_{1-3}$-alkyl and are in each case mono- or polysubstituted or unsubstituted; $OR^{13}$; $NR^{14}R^{15}$;
  $R^5$ represents =O; H; $COOR^{13}$, $CONR^{13}$, $OR^{13}$; $C_{1-5}$-alkyl, saturated or unsaturated, branched or unbranched, unsubstituted or mono- or polysubstituted; $C_{3-8}$-cycloalkyl, saturated or unsaturated, unsubstituted or mono- or polysubstituted; aryl-, or heteroaryl, unsubstituted or mono- or polysubstituted; or aryl, $C_{3-8}$-cycloalkyl or heteroaryl which are bonded via $C_{1-3}$-alkyl and are unsubstituted or mono- or polysubstituted;
  $R^6$ represents H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, saturated or unsaturated, branched or unbranched, unsubstituted or mono- or polysubstituted; $C_{3-8}$-cycloalkyl, saturated or unsaturated, unsubstituted or mono- or polysubstituted; aryl-, or heteroaryl, unsubstituted or mono- or polysubstituted; or aryl, $C_{3-8}$-cycloalkyl or heteroaryl which are bonded via $C_{1-3}$-alkyl and are unsubstituted or mono- or polysubstituted; or
  $R^5$ and $R^6$ together denote $(CH_2)_n$, where n =2, 3, 4, 5 or 6, wherein individual hydrogen atoms can also be replaced by F, Cl, Br, I, $NO_2$, $CF_3$, $OR^{13}$, CN or $C_{1-5}$-alkyl;
  $R^7$, $R^8$, $R^9$ and $R^{10}$ independently of one another represent H, F, Cl, Br, I, $NO_2$, $CF_3$, $OR^{13}$, $SR^{13}$, $SO_2R^{13}$, $SO_2OR^{13}$, $SO_2NH_2$ CN, $COOR^{13}$, $NR^{14}R^{15}$; $C_{1-5}$-alkyl, $C_{3-8}$-cycloalkyl, unsubstituted or mono- or polysubstituted; aryl-, or heteroaryl, unsubstituted or mono- or polysubstituted; or aryl, $C_{3-8}$-cycloalkyl or heteroaryl which are bonded via $C_{1-3}$-alkyl and are unsubstituted or mono- or polysubstituted;
  wherein
    $R^{13}$ denotes H; $C_{1-5}$-alkyl in each case saturated or unsaturated, branched or unbranched, unsubstituted or mono- or polysubstituted; $C_{3-8}$-cycloalkyl, in each case saturated or unsaturated, unsubstituted or mono- or polysubstituted; aryl-, or heteroaryl, unsubstituted or mono- or polysubstituted; or aryl, $C_{3-8}$-cycloalkyl or heteroaryl which are bonded via $C_{1-3}$-alkyl and are unsubstituted or mono- or polysubstituted;
    $R^{14}$ and $R^{15}$ independently denote H; $C_{1-5}$-alkyl, in each case saturated or unsaturated, branched or unbranched, unsubstituted or mono- or polysubstituted; or $C_{3-8}$-cycloalkyl, in each case saturated or unsaturated, unsubstituted or mono- or polysubstituted; aryl-, or heteroaryl, unsubstituted or mono- or polysubstituted; or aryl, $C_{3-8}$-cycloalkyl or heteroaryl which are bonded via $C_{1-3}$-alkyl and are unsubstituted or mono- or polysubstituted; or
    $R^{14}$ and $R^{15}$ together form $CH_2CH_2OCH_2CH_2$, $CH_2CH_2NR^{16}CH_2CH_2$ or $(CH_2)_{3-6}$,
    wherein
      $R^{16}$ denotes H; $C_{1-5}$-alkyl saturated or unsaturated, branched or unbranched, unsubstituted or mono- or polysubstituted;
  X represents O, S, SO or $SO_2$;
    wherein, with reference to alkyl, mono- or polysubstituted means substitution of one or more hydrogen radicals by F, Cl, Br, I, —CN, $NH_2$, NH-alkyl, NH-aryl, NH-heteroaryl, NH-cycloalkyl, NH-alkyl-aryl, NH-alkyl-heteroaryl, NH-alkyl-OH, $N(alkyl)_2$, $N(alkyl-aryl)_2$, $N(alkyl-heteroaryl)_2$, $N(cycloalkyl)_2$, N(alkyl-OH)$_2$, NO$_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, C(=O)C$_{1-6}$-alkyl, C(=S)C$_{1-6}$-alkyl, C(=O)aryl, C(=S)aryl, C(=O)C$_{1-6}$-alkyl-aryl, C(=S)C$_{1-6}$-alkyl-aryl, C(=O)-heteroaryl, C(=S)-heteroaryl, C(=O)-cycloalkyl, C(=S)-cycloalkyl, CO$_2$H, CO$_2$-alkyl, CO$_2$-alkyl-aryl, C(=O)NH$_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, SO-alkyl, SO$_2$-alkyl, SO$_2$NH$_2$, SO$_3$H, PO(O-C$_{1-6}$-alkyl)$_2$, Si(C$_{1-6}$-alkyl)$_3$, Si(C$_{3-8}$-cycloalkyl)$_3$, Si(CH$_2$-C$_{3-8}$-cycloalkyl)$_3$, Si(phenyl)$_3$, cycloalkyl or aryl on one or different atoms, and wherein, with reference to aryl, heteroaryl and cycloalkyl, mono- or polysubstituted means substitution of one or more hydrogen atoms of the ring system by F, Cl, Br, I, CN, NH$_2$, NH-alkyl, NH-aryl, NH-heteroaryl, NH-alkyl-aryl, NH-alkyl-heteroaryl, NH-cycloalkyl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, NO$_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, C(=O)C$_{1-6}$-alkyl, C(=S)C$_{1-6}$-alkyl, C(=O)aryl, C(=S)aryl, C(=O)-C$_{1-6}$-alkyl-aryl, C(=S)C$_{1-6}$-alkyl-aryl, C(=O)-heteroaryl, C(=S)-heteroaryl, C(=O)-cycloalkyl, C(=S)-cycloalkyl, CO$_2$H, CO$_2$-alkyl, CO$_2$-alkyl-aryl, C(=O)NH$_2$, C(=O)NH-alkyl, C(=O)NHaryl, C(=O)NH-cycloalkyl, C(=O)N(alkyl)$_2$, C(=O)N(alkyl=aryl)$_2$, C(=O)N(alkyl-heteroaryl)$_2$, C(=O)N(cycloalkyl)$_2$, S(O)-alkyl, S(O)-aryl, SO$_2$-alkyl, SO$_2$-aryl, SO$_2$NH$_2$, SO$_3$H, CF$_3$, =O, =S; alkyl, cycloalkyl, aryl or heteroaryl; on one or different atoms;

or a physiologically acceptable salt thereof; and at least one physiologically acceptable additive, auxiliary substance or further active compound.

2. A pharmaceutical composition according to claim 1, wherein in said spirocyclic cyclohexane compound:

W represents NR$^4$;

X denotes O;

R$^1$ and R$^2$ independently of one another denote H; C$_{1-4}$-alkyl, branched or unbranched, mono- or polysubstituted or unsubstituted; or CHO R$^3$ denotes (CH$_2$)n-aryl, in each case unsubstituted, monosubstituted or polysubstituted on the aryl group, where n=0-2;

R$^4$ denotes H; C$_{1-3}$-alkyl, mono- or polysubstituted or unsubstituted; or CO(CH$_2$)$_m$H, where m=0 to 2;

R$^5$ and R$^6$ in each case represent H; and

R$^7$, R$^8$, R$^9$ and R$^{10}$ independently of one another denote H; C$_{1-5}$-alkyl, OC$_{1-3}$-alkyl, in each case branched or unbranched, saturated or unsaturated, unsubstituted, monosubstituted or polysubstituted; F, Cl, Br, I, CF$_3$, OH, SH, SCH$_3$, OCH$_3$, NH$_2$, COOH, COOCH$_3$, NHCH$_3$, N(CH$_3$)$_2$, NO$_2$, SO$_3$H, SO$_2$NH$_2$, pyridyl or phenyl.

3. A pharmaceutical composition according to claim 2, wherein in said spirocyclic cyclohexane compound:

W represents NR$^4$;

X denotes O;

R$^1$ and R$^2$ each denote H or CH$_3$, with the proviso that R$^1$ and R$^2$ are not simultaneously H;

R$^3$ denotes phenyl;

R$^4$ denotes H;

R$^5$, R$^6$, R$^7$, R$^9$ and R$^{10}$ each represent H; and

R$^8$ denotes H; CH$_3$, OCH$_3$, F, Cl, Br, OH or NO$_2$.

4. A pharmaceutical composition according to claim 1, wherein said spirocyclic cyclohexane compound is selected from the group consisting of:

1,1-(3-dimethylamino-3-phenylpentamethylene)-1,3,4,9-tetrahydropyrano[3,4-b]indole hydrochloride, 1,1-(3-dimethylamino-3-phenylpentamethylene),1,3,4,9-tetrahydropyrano[3,4-b]indole hemicitrate, 1,1-(3-dimethylamino-3-phenylpentamethylene)-1,3,4,9-tetrahydro-2-thia-9-azafluorene hemicitrate, 1,1-(3-dimethylamino-3-phenylpentamethylene)-1,3,4,9-tetrahydro-2-thia-9azafluorene citrate, 1,1-(3-dimethylamino-3-phenylpentamethylene)-3,4-dihydro-1H-2-oxa-9-thiafluorene L-tartrate, 1,1-(3-dimethylamino-3-(4-fluorophenyl)pentamethylene)-3,4-dihydro-1H-2-oxa-9-thiafluorene triflate, 1,1-(3-dimethylamino-3-phenylpentamethylene)-3,4-dihydro-1H-2,9-dioxafluorene hemicitrate, 1,1-(3-dimethylamino-3-phenylpentamethylene)-6-methoxy-1,3,4,9-tetrahydropyrano[3,4-b]indole hydrochloride, 1,1-(3-dimethylamino-3-phenylpentamethylene)-3-methyl-1,3,4,9-tetrahydropyrano[3,4-b]indole citrate, 6-bromo-1,1-(3-dimethylamino-3-phenylpentamethylene)-3-methyl-1,3,4,9-tetrahydropyrano[3,4-b]indole hemicitrate, 1,1-(3-dimethylamino-3-phenylpentamethylene)-3-methyl-6-nitro-1,3,4,9-tetrahydropyrano[3,4-b]indole citrate, 6-chloro-1,1-(3-dimethylamino-3-phenylpentamethylene)- 3-methyl-1, 3,4,9-tetrahydropyrano[3,4-b]indole citrate, 3;9-dimethyl-1,1-(3-dimethylamino-3-phenylpentamethylene)-1,3,4,9-tetrahydropyrano[3,4-b]indole citrate, 1, 1-(3- dimethylamino-3-(4-fluorophenyl)pentamethylene)-1,3, 4,9,-tetra-hydro-pyrano[3,4-b]indole hemicitrate, 1,1-(3-dimethylamino-3-(3-fluorophenyl)pentamethylene)-1,3,4,9-tetra-hydro-pyrano[3,4-b]indole hemicitrate, 1,1-(3-dimethylamino-3-phenylpentamethylene)-6-fluoro-1,3,4,9-tetrahydropyrano[3,4-b]indole hemicitrate, 1,1-(3-dimethylamino-3-phenylpentamethylene)-6-methyl-1,3,4,9-tetrahydropyrano[3,4-b]indole hemicitrate, 1,1-(3-dimethylamino-3-phenylpentamethylene)-9-phenyl-1,3,4,9-tetrahydropyrano[3,4-b]indole citrate, 1,1-(3-methylamino-3-phenylpentamethylene)-1,3,4,9-tetrahydro-pyrano-[3,4-b]indole hemicitrate, 1,1-(3-dimethylamino-3-phenylpentamethylene)-6-fluoro-3-methyl-1,3,4,9-tetrahydro-pyrano-[3,4-b]indole hemicitrate, 3,6-dimethyl-1,1-(3-dimethylamino-3-phenylpentamethylene)-1,3,4,9-tetra-hydro-pyrano-[3,4-h]indole hemicitrate, 3,6-dimethyl-1,1-(3-dimethylamino-3-phenylpentamethylene)-1,3,4,9-tetra-hydro-pyrano-[3,4-b]indole citrate, 1, 1-(3-dimethylamino- 3-phenylpentamethylene)- 3-methyl-9-phenyl-1, 3, 4,9-tetrahydropyrano[3,4-b]indole citrate, 1,1-(3-dimethylamino-3-(4-fluorophenyl)pentamethylene)-1,3,4,9-tetra-hydro-2-thia-9-azafluorene methanesulfonate,
1,1-(3-dimethylamino-3-(3-fluorophenyl)pentamethylene)-1,3,4,9-tetra-hydro-2-thia-9-azafluorene methanesulfonate,
1,1-(3-dimethylamino-3-phenylpentamethylene)-3,4-dihydro-1H-9-oxa-2-thiafluorene citrate,
6,6-(3-dimethylamino-3-phenylpentamethylene)-1,2,3,4,4a,6,7,11c-octahydro-5-oxa-7-azabenzo[c]fluorene citrate,
1,1-(3-dimethylamino-3-phenylpentamethylene)-6-bromo-1,3,4,9-tetrahydropyrano[3,4-b]indole hemicitrate,
1,1-(3-dimethylamino-3-phenylpentamethylene)-1,3,4,9-tetrahydro-pyrano[3,4-b]indol-6-ol citrate,
1,1-(3-methylamino-3-phenylpentamethylene)-6-fluoro-1,3,4,9-tetrahydropyrano[3,4-b]indole hemicitrate,
1,1-(3-dimethylamino-3-(4-fluorophenyl)pentamethylene)-3,4-dihydro-1H-2,9-dithiafluorene methanesulfonate,
1,1-(3-dimethylamino-3-phenylpentamethylene)-3,4-dihydro-1H-2,9-dithiafluorene citrate, and
1,1-(3-dimethylamino-3-phenylpentamethylene)-2-oxo-1,3,4,9-tetrahydro-2-thia-9-aza-fluorene citrate.

5. A pharmaceutical composition according to claim 1, wherein said spirocyclic cyclohexane compound is 1,1-(3-dimethylamino-3-phenylpentamethylene)-6-fluoro-1,3,4,9-tetrahydropyrano[3,4-b]indole or a salt thereof with a physiologically acceptable acid.

6. A pharmaceutical composition according to claim 5, wherein said spirocyclic cyclohexane compound is present in the form of the more polar diastereomer.

7. A pharmaceutical composition according to claim 5, wherein said spirocyclic cyclohexane compound is present in the form of the more non-polar diastereomer.

8. A pharmaceutical composition according to claim 1, wherein said spirocyclic cyclohexane compound is 1,1-(3-methylamino-3-phenylpentamethylene)-6-fluoro-1,3,4,9-tetrahydropyrano[3,4-b]indole or a salt thereof with a physiologically acceptable acid.

9. A pharmaceutical composition according to claim 8, wherein said spirocyclic cyclohexane compound is present in the form of the more polar diastereomer.

10. A pharmaceutical composition according to claim 9, wherein said spirocyclic cyclohexane compound is present in the form of the more non-polar diastereomer.

\* \* \* \* \*